US006262124B1

(12) United States Patent
Dull et al.

(10) Patent No.: US 6,262,124 B1
(45) Date of Patent: *Jul. 17, 2001

(54) PHARMACEUTICAL COMPOSITIONS AND METHODS FOR USE

(76) Inventors: Gary Maurice Dull, 6025 Shallowford Rd., Lewisville, NC (US) 27023; Jared Miller Wagner, 3523 N. Roxboro St., Durham, NC (US) 27704; William Scott Caldwell, 1270 Yorkshire Rd., Winston-Salem, NC (US) 27106; Craig Harrison Miller, 1564 Sharon Rd., Winston-Salem, NC (US) 27103; Jeffrey Daniel Schmitt, 632 Laurel St., Winston-Salem, NC (US) 27101; Balwinder Singh Bhatti, 3740J Moss Dr., Winston-Salem, NC (US) 27106; Srishailkumar Basawannappa Hadimani, 5009 Eltha Dr. #E, Winston-Salem, NC (US) 27105

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,231

(22) Filed: Oct. 22, 1998

(51) Int. Cl.[7] ................................................ A01N 33/02
(52) U.S. Cl. ........................ 514/649; 514/654; 564/336; 564/305
(58) Field of Search ................................. 514/649, 654; 564/336, 305

(56) References Cited

U.S. PATENT DOCUMENTS

| 5,212,188 | * | 5/1993 | Caldwell et al. . |
| 5,597,919 | * | 1/1997 | Dull et al. . |
| 5,604,231 | * | 2/1997 | Smith et al. . |
| 5,612,331 | * | 3/1997 | Porter et al. . |
| 5,616,707 | * | 4/1997 | Crooks et al. . |
| 5,616,716 | * | 4/1997 | Dull et al. . |
| 5,661,185 | * | 8/1997 | Takaki et al. . |
| 5,663,356 | * | 9/1997 | Ruecroft et al. . |
| 5,726,316 | * | 3/1998 | Crooks et al. . |
| 5,731,314 | * | 3/1998 | Bencherif et al. . |
| 5,811,442 | * | 9/1998 | Bencherif et al. . |
| 5,824,692 | * | 10/1998 | Lippiello et al. . |
| 5,852,041 | * | 12/1998 | Cosford et al. . |
| 5,861,423 | * | 1/1999 | Caldwell et al. . |

FOREIGN PATENT DOCUMENTS

97/19059 * 5/1997 (WO) .

* cited by examiner

Primary Examiner—Paul J. Killos
(74) Attorney, Agent, or Firm—Myers Bigel Sibley & Sajove, P.A.

(57) ABSTRACT

Pharmaceutical compositions aryl substituted amine compounds, and in particular, 3-aminophenyl amine compounds are provided. Representative compounds are (E)-4-(3-aminophenyl)-3-buten-1-amine, (E)-N-methyl-4-(3-aminophenyl)-3-buten-1-amine and (E)-N-methyl-5-(3-aminophenyl)-4-penten-2-amine.

21 Claims, No Drawings

PHARMACEUTICAL COMPOSITIONS AND METHODS FOR USE

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al.,*J. Neurochem.* 43:1593 (1984); Rapier et al., *J. Neurochern.* 50:1123 (1988); Sandor et al., *Brain Res.* 567:313 (1991) and Vizi, *Br. J Pharmacol.* 47:765 (1973). Release of norepinephrine by neurons upon administration of nicotine has been reported by Hall et al., *Biochem. Pharmacol* 21:1829 (1972). Release of serotonin by neurons upon administration of nicotine has been reported by Hery et al., *Arch. Int. Pharmacoclyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic. S*40 (1994). Furthermore, various other beneficial pharmacological effects of nicotine have been proposed. See, Decina et al., *Biol. Psychiatry* 28:502 (1990); Wagner et al., *Pharmacolpsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a wide variety of conditions and disorders. See, for example, those types of conditions and disorders set forth in Williams et al. *DN&P* 7(4):205–227 (1994), Americ et al., *CNS Drug Rev.* 1(1):1–26 (1995), Arneric et al., *Exp. Opin. Invest. Drugs* 5(1): 79–100 (1996), Bencherifet al., *JPET* 279:1413–1421 (1996), Lippiello et al., *JPET* 279:1422–1429 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, PCT WO 97/19059, European Patent Application 857,725, and U.S. Pat. Nos. 5,278, 176 to Lin, 5,583,140 to Bencherifet al., 5,597,919 to Dull et al., 5,604,231 to Smith et al.,5,616,716 to Dull et al. and 5,811,442 to Bencherif et al.

Nicotinic compounds are reported as being particularly useful for treating a wide variety of Central Nervous System (CNS) disorders. CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, anxiolysis, attention deficit hyperactivity disorder, depression, dyslexia, epilepsy, Huntington's chorea, hyperkinesia, mania, neuro-endocrine disorders, schizophrenia, sleep disorders, tardive dyskinesia, Tourette's syndrome, and dysregulation of food intake.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS disorders) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to affect the functioning of the CNS, but which compound when employed in an amount sufficient to affect the functioning of the CNS, does not significantly affect those receptor subtypes which have the potential to induce undesirable side effects (e.g., appreciable activity at skeletal muscle and ganglia sites).

SUMMARY OF THE INVENTION

The present invention relates to aryl substituted amine compounds, and in particular, 3-aminophenyl amine compounds. Representative compounds are (E)-4-(3-aminophenyl)-3-buten-1-amine, (E)-N-methyl-4-(3-aminophenyl)-3-buten-1-amine, (E)-N-methyl-5-(3-aminophenyl)-4-penten-2-amine, 2-((3 -aminophenyl) methoxy)ethan-l-amine, I-((3-aminophenyl)methoxy) propan-2-amine and N-methyl-1-((3-aminophenyl) methoxy)propan-2-amine. The present invention also relates to methods for synthesizing certain aryl substituted amine compounds, such as the compounds of the present invention. The present invention also relates to prodrug derivatives of aryl substituted amine compounds of the present invention.

Compounds of the present invention exhibit activity at acetyicholine receptors, and are useful towards modulating release of ligands involved in neurotransmission. Compounds of the present invention are selective to certain nicotinic acetylcholine receptor subtypes, and can act as agonists at those receptor subtypes. Hence, the present invention relates to methods for modulating the activity of certain nicotinic acetylcholine receptor subtypes by administering a compound of the present invention.

The present invention also relates to methods for the prevention or treatment of a wide variety of conditions or disorders, and particularly those disorders characterized by dysfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention. The present invention also relates to methods for the treatment of Alzheimer's disease comprising coadministering certain aryl substituted amine compounds, such as the compounds of the present invention, with a cholinesterase inhibitor such as tacrine or donepezil.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptor sites (e.g., act as pharmacological agonists to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastrointestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds of the formula:

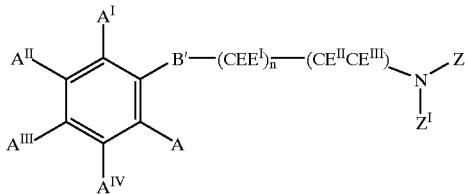

where A, $A^I$, $A^{II}$, $A^{III}$ and $A^{IV}$ are substituent species characterized as having a sigma m value greater than 0, often greater than 0.1, and generally greater than 0.2, and even greater than 0.3; less than 0 and generally less than −0.1; or 0; as determined in accordance with Hansch et al., *Chem. Rev.* 91:165 (1991). Preferably, each substituent species has a sigma m value which is between about −0.3 and about 0.75, and frequently is between about −0.25 and about 0.6, and individual substituent species can have a sigma m value of 0; B' is a substituted or unsubstituted two atom bridging species wherein at least one atom is carbon bonded to the benzene ring and the other atom is carbon, oxygen, nitrogen or sulfur; as such, B', can be

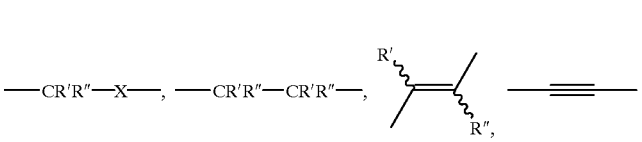

(e.g., alkyl-containing, olefinic or acetylinic linkage, unsubstituted or substituted) with X being oxygen, nitrogen or sulfur, and R' and R" being straight chain or branched alkyl (or R' and R" and the intervening atoms can combine to form a ring structure, such as cyclopropyl cyclobutyl, cyclopentyl, cyclohexyl, cycloheptyl, adamantyl or quinuclidinyl), with at least one of each of R' and R" being hydrogen preferred, and R' being hydrogen being especially preferred) and can be part of a substituted or unsubstituted cycloalkyl ring (e.g., cyclopropyl, cyclobutyl, cyclopentyl,); B', $A^I$ and the associated carbon atoms can combine to form a ring structure (e.g., a 5 or 6 membered ring); B' and E and the intervening atoms can combine to form a ring structure (e.g., cycloalkyl, substituted cycloalkyl, heterocyclyl, substituted heterocyclyl); n is an integer from 0 to 5, preferably 1, 2 or 3, more preferably 1 or 2, and most preferably 1; E, $E^I$, $E^{II}$ and $E^{III}$ individually represent hydrogen, alkyl (e.g., straight chain or branched alkyl including $C_1$–$C_8$, preferably $C_1$–$C_5$, such as methyl, ethyl, or isopropyl), substituted alkyl, halo substituted alkyl (e.g., straight chain or branched alkyl including $C_1$–$C_8$, preferably $C_1$–$C_5$, such as trifluoromethyl or trichloromethyl), cycloalkyl, substituted cycloalkyl, heterocyclyl, substituted heterocyclyl, aryl, substituted aryl, alkylaryl, substituted alkylaryl, arylalkyl or substituted arylalkyl; all of E, $E^I$, $E^{II}$, $E^{III}$ can be hydrogen, or at least one of E, $E^I$, $E^{II}$, $E^{III}$ is non-hydrogen (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl) and the remaining E, E', E'', E''' are hydrogen, either E and E'' or E' and E''' and their associated carbon atom can combine to form a ring structure such as cyclopentyl, cyclohexyl or cycloheptyl; either E and E'' or E' and E''' and their associated carbon atoms can combine to form a ring structure such as cyclopentyl, cyclohexyl or cycloheptyl; Z and Z' individually represent hydrogen, alkyl (e.g., straight chain or branched alkyl including $C_1$–$C_8$, preferably $C_1$–$C_5$, such as methyl, ethyl, or isopropyl), substituted alkyl, acyl, alkoxycarbonyl, or aryloxycarbonyl and preferably at least one of Z and Z' is hydrogen, and most preferably Z is hydrogen and Z' is methyl; alternatively Z is hydrogen and Z' represents a ring structure (cycloalkyl, heterocyclyl or aryl), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl, thiazolyl or oxazolyl (where any of the foregoing can be suitably substituted with at least one substituent group, such as alkyl, alkoxyl, halo, or amino substituents); alternatively Z is hydrogen and Z' is propargyl; alternatively Z, Z', and the associated nitrogen atom can form a ring structure such as aziridinyl, azetidinyl, pyrrolidinyl, piperidinyl,, morpholinyl, 2-imino–2,3-dihydrothiazolyl or 2-imino-2,3-dihydrooxazolyl, and in certain situations, piperazinyl (e.g., piperazine); Z' and E' and the associated carbon and nitrogen atoms can combine to form a monocyclic ring structure such as azetidinyl, pyrrisoxazolaminylridinyl, piperazinyl, pyrazolyl or isoxazolaminyl; however it is preferred that when Z' and E' and the associated carbon and nitrogen atoms combine to form such a ring, neither E' nor E''' are substituted or unsubstituted aryl, heteroaryl, benzhydryl or benzyl; Z' and E''' and the associated carbon and nitrogen atoms can combine to form a monocyclic ring structure such as azetidinyl, pyrrolidinyl, piperidinyl, or piperazinyl or a bicyclic ring structure such as 3-(2-azabicyclo[4.2.0]octyl), 3-(2-azabicyclo[2.2.2]octyl), or 3-(2-azabicyclo[2.2.1]heptyl); Z, Z' and E''' and the associated carbon and nitrogen atoms can combine to form a bicyclic ring structure such as quinuclidinyl, 2-(1-azabicyclo[2.2.1]-heptyl), or 2-(1-azabicyclo[3.3.0]octyl), or a tricyclic ring structure such as azaadamantyl; Z', E'' and E''' and the associated carbon and nitrogen atoms can combine to form a bicyclic ring structure such as 1-(2-azabicyclo[2.2.1]heptyl); Z, Z', E'' and E''' and the associated carbon and nitrogen atoms can combine to form a tricyclic ring structure. More specifically, A, A', A'', A''' and A$^{IV}$ include H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, $SCH_3$, $N_3$, $SO_2CH_3$, OR', $(CR'R")_qOR'$, O—$(CR'R")_qC_2R'$, SR', C(=O)NR'R", NR'C(=O)R", C(=O)R', $(CR'R")_qC_2R'$, C(=O)OR', OC(=O)R', OC(=O)NR'R" and NR'C(=O)OR" where q is an integer from 1 to 6 and R' and R" are individually hydrogen or alkyl (e.g., $C_1$–$C_{10}$ alkyl, preferably $C_1$–$C_5$ alkyl, and more preferably methyl, ethyl, isopropyl or isobutyl), cycloalkyl (e.g., cyclopropyl cyclobutyl, cyclopentyl, cyclohexyl, cycloheptyl, and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrrolidinyl, and piperidinyl), an aromatic group-containing species (e.g., pyridyl, quinolinyl, pyrimidinyl, furanyl, phenyl, and benzyl where any of the foregoing can be suitably substituted with at least one substituent group, such as alkyl, alkoxyl, halo, or amino substituents). Other representative aromatic ring systems are set forth in Gibson et al., *J Med. Chem.* 39:4065 (1996). Typically, A$^{IV}$ includes NR'R", OR' and $NO_2$ where R' and R" are as defined above. Preferably, A$^{IV}$ is $NH_2$, $NHCH_3$ or $N(CH_3)_2$, with $NH_2$ being most preferred. Adjacent substituents A, A', A'', A''' and A$^{IV}$ can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities. In addition, it is highly preferred that A is hydrogen and it is preferred that A' is hydrogen. Preferably, E, E' and E'' are hydrogen. In one preferred embodiment, n is 1 or 2, E, E' and E'' each are hydrogen, and E''' is alkyl (e.g., methyl). In another preferred embodiment, n is 1 or 2 and E, E', E'', E''' each are hydrogen. Depending upon the identity and positioning of each individual E, E', E'' and E''', certain compounds can be optically active. Additionally, compounds of the present invention can have chiral centers within the side chain (e.g., the compound can have an R or S configuration). Depending upon E, E', E'' and E''', compounds of the present invention have chiral centers, and the present invention relates to racemic mixtures of such compounds as well as single enantiomers. Typically, the selection of n, E, E', E'', and E''' is such that up to about 4, and frequently up to 3, and usually 0, 1 or 2, of the substituents designated as E, E', E'' and E''' are non-hydrogen substituents (i.e., substituents such as alkyl or halo-substituted alkyl). Typically, it is preferred that A'' is H, Br or OR', where R' preferably is methyl, ethyl, isopropyl, isobutyl or tertiary butyl.

As employed herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "cycloalkyl" refers to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above; "acyl" refers to straight chain or branched alkyl- or substituted alkyl-carbonyl radicals including $C_1$–$C_8$, preferably $C_1$–$C_5$, such as formyl, acetyl, or propanoyl; "alkoxycarbonyl" refers to an alkyl or substituted alkyl radical attached to an O-carbonyl moiety; and "aryloxycarbonyl" refers to an aryl or substituted aryl radical attached to an O-carbonyl moiety.

Of particular interest are compounds of the formula:

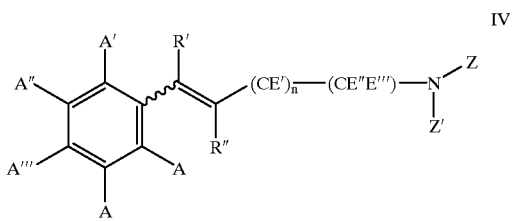

where $A^{IV}$ is NR'R", OR' and $NO_2$, A, A', A", A''', E, E', E'', E''', R', R", Z and Z' are as defined hereinbefore and where the wavy line in the structure indicates that the compound can have the cis (Z) or trans (E) form. Preferably, $A^{IV}$ is $NH_2$, $NHCH_3$ or $N(CH_3)_2$, with $NH_2$ being most preferred. Typically, the compound has the trans (E) form, R' and R" both are hydrogen, E, E' and E'' each are hydrogen, E''' is hydrogen or lower alkyl, Z is hydrogen or methyl, and Z' is hydrogen.

Also of particular interest are compounds of the formula:

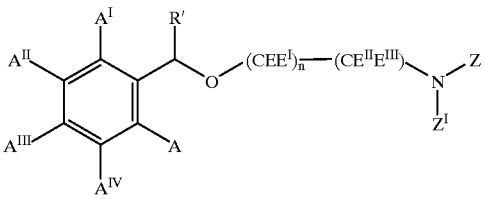

where $A^{IV}$ is NR'R", OR' and $NO_2$ and A, A', A", A''', E, E', E'', E''', R', R", Z and Z' are as defined hereinbefore. Preferably, $A^{IV}$ is $NH_2$, $NHCH_3$ or $N(CH_3)_2$, with $NH_2$ being most preferred. Typically, R' is hydrogen, E, E' and E'' each are hydrogen, E''' is hydrogen or lower alkyl, Z is hydrogen or methyl, and Z' is hydrogen.

The methods by which compounds of the present invention can be synthetically produced can vary. Certain aryl substituted olefinic amine compounds can be prepared using a palladium catalyzed coupling reaction of an aromatic halide and a terminal olefin containing a protected amine substituent (e.g., phthaloyl, benzoyl, or tert-butoxycarbonyl protecting groups), removal of the protective group to obtain a primary amine, and optional alkylation to provide a secondary or tertiary amine. In particular, certain compounds, such as (E)-4-(3-aminophenyl)-3-buten-1-amine can be prepared by subjecting a 3-halo-substituted aniline compound such as 3-bromoaniline or 3-iodoaniline (commercially available from Aldrich Chemical Company and Lancaster Synthesis, Inc.) to a palladium catalyzed Heck coupling reaction using an olefin possessing a protected amine functionality (e.g., such an olefin provided by the reaction of a phthalimide salt with 4-halo-1-butene), followed by removal of the phthaloyl protecting group with methylamine or hydrazine.

Typically, the types of procedures set forth in W. C. Frank et al., *J. Org Chem.* 43: 2947 (1978) and N. J. Malek et al., *J. Org. Chem.* 47: 5395 (1982) involving a palladium-catalyzed coupling of an olefin and an aromatic halide are used. In a similar manner, other compounds can be prepared by the Heck reaction of 3-halo-substituted aniline compounds with an olefin containing a protected amine functionality, (such as provided by the reaction of a phthalimide salt with 3-halo-1-propene, 5-halo-1-pentene or 6-halo-1-hexene), followed by removal of the phthaloyl protecting group with methylamine or hydrazine. Primary amines, produced in these procedures, may be alkylated by sequential reaction with di-tert-butyl dicarbonate (to give the N-tert-butoxycarbonyl derivatives), and followed by reaction with sodium hydride and an alkyl halide (e.g., methyl iodide, benzyl bromide, propargyl bromide) in N,N-dimethylformamide, as described by Dull in U.S. Pat. No. 5,597,919. Removal of the tert-butoxycarbonyl group with trifluoroacetic acid will give the secondary amine (i.e., the corresponding N-methyl, N-benzyl, or N-propargyl derivative).

In a similar approach, other compounds such as (E)-N-methyl-4-(3-aminophenyl)-3-buten-1-amine can be prepared by subjecting a 3-halo-substituted aniline such as 3-bromoaniline or 3-iodoaniline to a palladium catalyzed coupling reaction with an olefin possessing a protected amine functionality (e.g., such as N-methyl-N-(3-buten-1-yl)benzamide), followed by removal of the benzoyl protecting group with aqueous acid. The required olefin can be prepared by reacting 4-bromo-1-butene with an excess of condensed methylamine in N,N-dimethylformamide in the presence of potassium carbonate to give N-methyl-3-buten-1-amine. Treatment of the latter compound with benzoyl chloride in dichloromethane containing triethylamine affords the olefinic side chain, N-methyl-N-(3-buten-1-yl)benzamide.

In another approach, other compounds such as (E)-N-methyl-4-(3-aminophenyl)-3-buten-1-amine can be prepared by subjecting a 3-halo-substituted aniline such as 3-bromoaniline or 3-iodoaniline to a palladium catalyzed coupling reaction with an olefin possessing a protected amine functionality (e.g., such as N-methyl-N-(tert-butoxycarbonyl)-3-buten-1-amine), followed by removal of the tert-butoxycarbonyl protecting group with trifluoroacetic acid. The required olefin, N-methyl-N-(tert-butoxycarbonyl)-3-buten-1-amine can be prepared by reacting 4-bromo-1-butene with an excess of condensed methylamine in N,N-dimethylformamide in the presence of potassium carbonate to give N-methyl-3-buten-1-amine. The latter compound can be treated with one equivalent of di-tert-butyldicarbonate in tetrahydrofuran to give N-methyl-N-(tert-butoxycarbonyl)-3-buten-1-amine.

The manner in which certain aryl substituted olefinic amine compounds possessing a branched side chain, such as (E)-N-methyl-5-(3-aminophenyl)-4-penten-2-amine, are provided can vary. By using one synthetic approach, the compound can be synthesized in a convergent manner, in which the side chain, N-methyl-N-(tert-butoxycarbonyl)-4-penten-2-amine is coupled with a 3-halo-substituted aniline, such as 3-bromoaniline (N-protected with the phthaloyl group), under Heck reaction conditions, followed by removal of the tert-butoxycarbonyl protecting group with trifluoroacetic acid and then removal of the phthaloyl protecting group with methylamine. The required olefin, N-methyl-N-(tert-butoxycarbonyl)-4-penten-2-amine can be prepared by treatment of commercially available 4-penten-2-ol (Aldrich Chemical Company, Lancaster Synthesis Inc) with p-toluenesulfonyl chloride in pyridine to afford 4-penten-2-ol p-toluenesulfonate, previously described by T. Michel, et al., *Liebigs Ann.* 11: 1811 (1996). The resulting tosylate can be converted to N-methyl-4-penten-2-amine by heating with excess methylamine. The latter amine, previously mentioned by A. Viola et al., *J Chen. Soc. Chem. Commun.* (21): 1429 (1984), can be converted to the olefinic amine side chain, N-methyl-N-(tert-butoxycarbonyl)-4-penten-2-amine by treatment with di-tert-butyl dicarbonate in dry tetrahydrofuran.

The aniline nitrogen can also be alkylated using the coupling method of O. Mitsunobu, *Synthesis:* 1 (1981). Any primary or secondary alcohol, including those containing other functional groups, may be used in the coupling. As an example, reaction of 3-bromoaniline with 3-quinuclidinol (Aldrich Chemical Company) in the presence of triphenylphosphine and diethyl azodicarboxylate will result in the formation of 3-bromo-N-(3-quinuclidinyl)aniline, which can be used in Heck couplings as described above.

Using the previously described synthetic methods involving the Heck reaction, certain N-alkyl-3-aminophenyl substituted olefinic amine compounds such as (E)-N-methyl-4-(N-methyl-3-aminophenyl)-4-buten-1-amine can be prepared starting from 3-halo-N-alkylanilines such as 3-iodo-N-methyl-aniline. The latter compound can be prepared from commercially available 3-iodoaniline (Aldrich Chemical Company, Lancaster Synthesis, Inc.) using the techniques of S. Padmanabhan et al., *Synth. Commun.* 27:691–699 (1997). 3-Iodoaniline can be monomethylated using trimethyl orthoformate in the presence of concentrated sulfuric acid followed by acid hydrolysis to give 3-iodo-N-methyl-aniline. Certain N,N-dialkyl-3-aminophenyl substituted olefinic amine compounds such as (E)-N-methyl-4-(N,N-dimethyl-3-aminophenyl)-4-buten-1-amine can be prepared starting from 3-bromo-N,N-dimethyl-aniline, which is commercially available from Karl Industries and Lancaster Synthesis, Inc.

Alternatively, an olefinic alcohol, such as 3-buten-1-ol, can be condensed with an aromatic halide, such as 3-bromoaniline or 3-iodoaniline. Protection of the nitrogen functionality of the aniline compound can be provided by a phthaloyl protecting group, using phthalic anhydride. Typically, the types of procedures set forth in Frank et al., *J. Org. Chem.* 43: 2947–2949 (1978) and Malek et al., *J. Org. Chem.* 47: 5395–5397 (1982) involving a palladium-catalyzed coupling of an olefin and an aromatic halide are used. The olefinic alcohol optionally can be protected as a tert-butyldimethylsilyl ether prior to the coupling. Desilylation then produces the olefinic alcohol. The alcohol condensation product then is converted to an amine using the type of procedures set forth in deCosta et al., *J. Org. Chem.*, 35: 4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-I-hepten-4-ol, 4-methyl-5-hexen-2-ol, 5-methyl-5-hexen-2-ol, 5-hexen-2-ol and 5-methyl-5-hexen-3-ol. Trifluoromethyl-substituted olefinic alcohols, such as 1,1,1-trifluoro-4-penten-2-ol, can be prepared from 1-ethoxy-2,2,2-trifluoroethanol and allyltrimethylsilane using the procedures of Kubota et al., *Tetrahedron Lett.* 33(10): 1351–1354 (1992), or from trifluoroacetic acid ethyl ester and allyltributylstannane using the procedures of Ishihara et al., *Tetrahedron Lett.* 34(56): 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amidation (e.g., by treatment using an alkyl amine and sodium cyanoborohydride). Typically, substituent groups of such 3-halo-aniline-type compounds are such that those groups can survive contact with those chemicals (e.g., tosyl chloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality.

Certain 5-alkoxy-3-aminophenyl substituted olefinic amine compounds of the present invention such as (E)-N-methyl-5-(5-methoxy-3-aminophenyl)- 4-penten-2-amine, can be synthesized by coupling a 3-halo-5-alkoxyaniline such as 3-bromo-5-methoxyaniline or 3-iodo-5-methoxyaniline (protected by a phthaloyl functionality) with an olefin containing a secondary alcohol functionality, 4-penten-2-ol, under Heck reaction conditions. The resulting secondary alcohol intermediate can be converted to its p-toluenesulfonate ester, followed by treatment with methylamine (which also removes the protecting group). Alternatively, certain 5-alkoxy-3-aminophenyl substituted olefinic amine compounds can be synthesized by coupling a 3-halo-5-alkoxyaniline such as 3-bromo-5-methoxyaniline or 3-iodo-5-methoxyaniline (protected by a phthaloyl functionality) with an olefinic side chain compound, such as N-methyl-N-(tert-butoxycarbonyl)-4-penten-2-amine, followed by removal of the protecting groups. The required 3-halo-5-alkoxyaniline compounds such as 3-bromo-5-methoxyaniline and 3-iodo-5-methoxyaniline can be prepared using the techniques of T. A. Emokpae et al., *J. Chem. Soc., Perkin Trans* 2 (1):14–17 (1977) and B. Liedholm, *Acta Chem. Scand., Ser. B* 38:877–884 (1984). In the former method, 3-bromo-5-methoxyaniline and 3-iodo-5-methoxyaniline can be prepared starting from commercially available 1,3,5-trinitrobenzene. Treatment of the latter compound with refluxing sodium methoxide produces 3,5-dinitroanisole. One of the nitro groups is then reduced to give 3-methoxy-5-nitroaniline. The latter compound can be diazotized and treated with copper(I) bromide to give 1-bromo-3-methoxy-5-nitrobenzene. Reduction with tin and hydrochloric acid gives 3-bromo-5-methoxyaniline. In a similar manner, 3-iodo-5-methoxyaniline can be prepared by diazotizing 3-methoxy-5-nitroaniline to give 1-iodo-3-methoxy-5-nitrobenzene. The latter compound can be reduced with iron filings and hydrochloric acid to give 3-iodo-5-methoxyaniline. Other 3-halo-5-alkoxyanilines such as 3-bromo-5-ethoxyaniline, 3-bromo-5-isopropoxyaniline, and 3-bromo-5-sec-butoxyaniline can be prepared using similar techniques. As such, compounds of the present invention such as (E)-N-methyl-5-(5-ethoxy-3-aminophenyl)-4-penten-2-amine, (E)-N-methyl-5-(5-isopropoxy-3-aminophenyl)-4-penten-2-amine, and (E)-N-methyl-5-(5-sec-butoxy-3-aminophenyl)-4-penten-2-amine can be similarly prepared.

The manner in which optically active forms of certain aryl substituted olefinic amine compounds, such as (2S)-(4F)-N-methyl-5-(3-aminophenyl)-4 -penten-2-amine, are provided can vary. In one synthetic approach, such compounds can be synthesized by coupling a halo-substituted aniline, 3-bromoaniline (which is protected with an appropriate protecting group, such as a phthaloyl group), with an olefin possessing a chiral, secondary alcohol functionality, (2R)-4-penten-2-ol, under fleck reaction conditions (acetonitrile-triethylamine (1:1, v/v) using a catalyst consisting of 1 mole % palladium(II) acetate and 4 mole % tri-o-tolylphosphine). The resulting chiral alcohol intermediate, (2R)-(4E)-5-(N-phthaloyl-3-aminophenyl)-4-penten-2-ol can be converted to its corresponding p-toluenesulfonate ester, which can be subsequently treated with excess methylamine, resulting in tosylate displacement with inversion of configuration to give the chiral amine, (2S)-(4E)-N-methyl-5-(3-aminophenyl)-4-penten-2-amine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at low temperatures (−25 to −10° C.) using the general synthetic methodology of Kalivretenos et al., *J. Org. Chem.* 56: 2883 (1991), to afford (2R)-4-penten-2-ol.

In a similar manner, the corresponding aryl substituted olefinic amine enantiomer, such as (2R)-(4E)-N-methyl-5-(can be synthesiznyl)-4-penten-2-amine, can be synthesized by the Heck coupling of 3-bromoaniline and (2S)-4-penten-2-ol. The resulting intermediate, (2S)-(4E)-5-(3-aminophenyl)-4-penten-2-ol, can be converted to its p-toluenesulfonate, which is subjected to methylamine displacement. The chiral alcohol, (2S)-4-penten-2-ol, can be prepared from (S)-(−)-propylene oxide (commercially available from Aldrich Chemical Company) using a procedure analogous to that described for the preparation of (2R)-4-penten-2-ol from (R)-(+)-propylene oxide as reported by Kalivretenos et al., *J. Org. Chem.* 56: 2883 (1991).

Certain aryl substituted olefinic amine compounds of the present invention can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and an alkyl lithium such as butyl lithium. The resulting N-protected aryl ketone is then chemically reduced to the corresponding alcohol, converted to the alkyl halide, mesylate or tosylate, and subsequently dehydrohalogenated or otherwise eliminated to introduce the olefin functionality. Removal of the N-protecting group then affords the desired compound.

Alternatively, the aryl substituted olefinic amine compounds of the present invention can be prepared by coupling an N-protected aminoaldehyde, such as 4-(N-methyl-N-(tert-butoxycarbonyl)amino)pentanal with an aryllithium. The required aldehyde can be prepared according procedure described by Otsuka et al., *J. Am Chem. Soc.* 112: 838–845 (1990), starting from commercially available 1,5-dimethyl-2-pyrrolidinone (Aldrich Chemical Company). Thus, heating 1,5-dimethyl-2-pyrrolidinone with 6N hydrochloric acid forms 4-(methylamino)pentanoic acid, which can be readily esterified to ethyl 4-(methylamino)pentanoate. The latter compound can be treated with one equivalent of di-tert-butyl dicarbonate to give ethyl 4-(N-methyl-N-(tert-butoxycarbonyl)amino)pentanoate which is then reduced with DIBAL-H to give 4-(N-methyl-N-(tert-butoxycarbonyl)amino)pentanal. Reaction of this aldehyde with an aryllithium will generate an alcohol, which can subsequently be converted to the N-protected olefinic amine by the procedures mentioned above (conversion of the alcohol to the halide and subsequent dehydrohalogenation). Removal of the tert-butoxycarbonyl protecting group affords the desired (E)-5-aryl-4-penten-2-amine. Suitably protected 3-haloanilines can be used as precursors of the aryllithiums required for this process, as described by Guijarro et al., *Tetrahedron* 49: 469–82 (1992) and by Gross et al., *J. Org. Chem.* 58, 2104–9 (1993). Thus 3-chloroaniline can be treated sequentially with pivaloyl chloride. n-butyllithium, and lithium in the presence of catalytic naphthalene to give a pivaloyl protected 3-(aminophenyl)lithium. This aryllithium, upon condensation with 4- (N-methyl-N-(tert-butoxycarbonyl)amino)pentanal and subsequent conversion of the alcohol into the alkene (as described above) and removal of the protecting groups, gives (E)-N-methyl-5-(3-aminophenyl)-4-penten-2-amine.

Aryl substituted olefinic amines of the present invention may contain azacyclic functionality, such as pyrrolidine or quinuclidine. The methods of synthesis of such compounds may vary. In one method, a Heck coupling can be used to attach a vinyl or allyl substituted nitrogen heterocycle to a 3-haloaniline. Thus N-(tert-butoxycarbonyl)-2-allylpyrrolidine and 3-bromoaniline can be coupled under conditions described by W. C. Frank et al., *J. Org. Chem.* 43: 2947 (1978) and N. J. Malek et al., *J. Org. Chem.* 47: 5395 (1982) involving palladium catalysis. Removal of the protecting group, using trifluoroacetic acid, will give 2-(I-(3-aminophenyl)propen-3-yl)pyrrolidine. The requisite N-(tert-butoxycarbonyl)-2-allylpyrrolidine can be made from commercially available 2-pyrrolidinemethanol (Aldrich Chemical Company). Treatment of 2-pyrrolidinemethanol with di-tert-butyl dicarbonate results in protection of the amine as its tert-butoxycarbonyl derivative. Subsequent reaction with p-toluenesulfonyl chloride in pyridine, followed by sodium iodide in acetone, gives 2-(iodomethyl)-N-(tert-butoxycarbonyl)pyrrolidine. This can be coupled with vinylmagnesium in the presence of cuprous iodide to give N-(tert-butoxycarbonyl)-2-allylpyrrolidine. The use of enantiomerically pure 2-pyrrolidinemethanol (both R and S isomers are available from Aldrich Chemical Company) results in the production of the single enantiomer of N-(tert-butoxycarbonyl)-2-allylpyrrolidine.

Likewise, 2-allylquinuclidine can be coupled with 3-bromoaniline, under Heck conditions, to give 2-(1-(3-aminophenyl)propen-3-yl)quinuclidine. The required 2-allylquinuclidine can be produced from 3-quinuclidinone (Aldrich Chemical Company) by alkylation and deoxygenation. Thus, 3-quinuclidinone is converted into its isopropylimine with isopropylamine and molecular sieves. Treatment of the imine with lithium diisopropylamide and allyl bromide, followed by hydrolysis, gives 2-allyl-3-quinuclidinone. Deoxygenation, by conversion of the ketone into its p-toluenesulfonylhydrazone and reduction with sodium borohydride, gives 2-allylquinuclidinone.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-aminopheniyl)-4-butyn-2-amine-type compound) using commercially available Lindlar catalyst (Aldrich Chemical Company) using the methodology set forth in H. Lindlar et al., *Org. Syn.* 46: 89 (1966). The requisite alkynyl compounds can be prepared by the palladium catalyzed coupling of an aromatic halide, preferably a 3-bromoaniline-type or a 3-iodoaniline-type compound with an alkynyl side chain compound (e.g., an N-methyl-4-pentyn-2-amine-type compound). Typically the methodology set forth in L. Bleicher et al., *Synlett.* 1115 (1995) is used for the palladium catalyzed coupling of an aryl halide with a monosubstituted alkyne in the presence of copper(I) iodide and triphenylphosphine and potassium carbonate as a base. Alkynyl compounds such as N-methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The manner in which aryl substituted acetylenic amine compounds of the present invention are synthetically produced can vary. For example, an aryl substituted acetylenic amine compound, such as an N-methyl-4-(3,4-dimethoxyphenyl)-3-butyn-1-amine type compound, can be prepared using a number of synthetic steps: (i) conversion of 3,4-dimethoxybenzaldehyde to a 1,1-dihalo-2-(3,4-dimethoxyphenyl)-ethylene using a carbon tetrahalide and triphenylphosphine, (ii) side chain elaboration of this intermediate by reaction with butyl lithium and ethylene oxide, affording 4-(3,4-dimethoxyphenyl)-3-butyn-1-ol, (iii) conversion of this intermediate to its methanesulfonate ester or p-toluenesulfonate ester, and (iv) mesylate or tosylate displacement with methyl amine, affording an N-methyl-4-(3,4-dimethoxyphenyl)-3-butyn-1-amine type compound. Representative alkylene oxides which can be employed either in racemic or optically active form include propylene oxide, 1,2-epoxybutane, 1,2-epoxypentane, 1,2-epoxyhexane, (E)-2,3-epoxybutane, and (Z)-2,3-epoxybutane. Other substituted benzaldehydes, such as 3-methoxybenzaldehyde, can be employed and other substituted aromatic aldehydes can be used. By the controlled hydrogenation of the alkynyl compounds using commercially available Lindlar catalyst using the methodology previously described, the (Z)-isomers of aryl substituted olefinic amine compounds can be obtained.

Compounds of the present invention, with alkyl or aryl substitution on one or both of the olefinic carbons, can be made by a variety of methods. For instance, the Wittig reaction of an alkyl aryl ketone with an (aminoalkyl) triphenylphosphonium yield will give an aryl substituted alkenamine. In one illustration of this chemistry, (3-bromopropyl)triphenylphosphonium bromide (Aldrich Chemical Company) can be reacted with a variety of primary and secondary amines to give the (3-(N-alkylamino) propyl)triphenylphosphonium bromides and (3-(N,N-dialkylamino)propyl)triphenylphosphonium bromides. These can be treated with n-butyllithium to generate the corresponding ylides which are then reacted with ketones to give substituted alkenamines, as described by Tretter et al. in U.S. Pat. No. 3,354,155 (1967). Thus stepwise treatment of(3-bromopropyl)triphenylphosphonium bromide with methylamine, n-butyllithium, and phthaloyl protected 3-aminoacetophenone (Aldrich Chemical Company) produces the phthaloyl protected N-methyl-4-(3-aminophenyl)-3-penten-1-amine. Removal of the phthaloyl protecting group using hydrazine hydrate will produce N-methyl-4-(3-aminophenyl)-3-penten-1-amine. In general, mixtures of E and 7 isomers generated by such Wittig reactions are separable by chromatographic methods.

Another method by which branched olefinic compounds of the present invention (i.e., those with alkyl or aryl substitution on one or both of the olefinic carbons) can be made is by the reaction of aryllithiums with various aminoketones, protected when necessary as their N-tert-butoxycarbonyl derivatives. The required protected aminoketones are produced from the commercially available haloketones by sequential process involving (i) reaction of a haloketone with ethylene glycol and p-toluenesulfonic acid (to produce the ethylene ketal), (ii) reaction of the haloketone ethylene ketal with a primary or secondary amine in N,N-dimethylformamide (to convert the halides into their corresponding secondary and tertiary amines), (iii) protection of the amino functionality by treatment with di-tert-butyl dicarbonate (to convert secondary amines into their N-tert-butoxycarbonyl derivatives), and (iv) treatment with pyridinium p-toluenesulfonate in acetone (to remove the ketal protecting group from the ketone). Alternatively the ethylene ketal can be removed by any of a variety of methods designed to retain other functionality, such as that described by Huet et al., Synthesis 63 (1978). Thus, 5-chloro-2-pentanone (Aldrich Chemical Company) and methylamine can be converted by the above reaction sequence into N-methyl-N-(tert-butoxycarbonyl)-5-amino-2-pentanone. Subsequent reaction of this protected aminoketone with a lithiated N-protected aniline, such as those described by Guijarro et al., *Tetrahedron* 49: 469–82 (1992) and by Gross et al., *J. Org. Chem.* 58: 2104–9 (1993), will afford an alcohol which can be converted to the alkene (mixture of E and Z isomers). Deprotection gives a mixture of E and Z isomers of N-methyl-4-(3-aminophenyl)-3-penten-1-amine.

The manner in which certain aryl substituted aliphatic amine compounds of the present invention are synthetically produced can vary. Preparation of various aryl substituted aliphatic amine compounds can be carried out using the types of techniques similar to those disclosed by L. Rondahl, *Acta Pharm. Suec.* 13: 229–234 (1976). For example, an N-methyl-4-(3-aminophenyl)-3-butan-1-amine type compound can be prepared by the reaction of methylamine with the chloro-intermediate, 1-chloro-4-(3-aminophenyl)-butane (or its hydrochloride salt). The latter compound can be obtained by treating 4-(3-aminophenyl)-butan-1-ol with thionyl chloride. The aliphatic alcohol, 4-(3-aminophenyl)-butan-1-ol can be prepared from the Heck reaction of 3-bromoaniline and 3-buten-1-ol, followed by hydrogenation of the olefinic intermediate, 4-(3-aminophenyl)-3-buten-1-ol. In another apporach, certain aryl substituted aliphatic amine compounds that possess a saturated side chain rather than an unsaturated side chain can be prepared by hydrogenation of the corresponding aryl substituted olefinic amine compounds or the corresponding acetylenic precursors. Hydrogenation procedures similar to those described by Kamimura et al., *Agr. Biol. Chem.* 27 (10): 684–688 (1963) can be used.

The manner in which certain aryl substituted olefinic amine compounds, such as (E)-N-methyl-5-(3-methoxyphenyl)-4-penten-2-amine, are provided can vary. By using one synthetic approach, the compound can be synthesized in a convergent manner, in which either 3-bromoanisole or 3-iodoanisole (commercially available from Aldrich Chemical Company or Lancaster Synthesis, Inc.) is coupled with the previously described side chain compound, N-methyl-N-(tert-butoxycarbonyl)-4-penten-2-amine under Heck reaction conditions, followed by removal of the tert-butoxycarbonyl protecting group with a strong acid such as trifluoroacetic acid. In a similar manner, (E)-N-methyl-4-(3-methoxyphenyl)-3-buten-I-amine can be prepared by the Heck coupling reaction of a 3-halo-anisole with the previously mentioned side chain compound, N-methyl-N-(tert-butoxycarbonyl)-3-buten-1-amine, followed by removal of the tert-butoxycarbonyl protecting group with a strong acid such as trifluoroacetic acid.

Certain commercially available fused polycyclic haloaromatics can be used to make the corresponding olefinic amine compounds using the previously described Heck reaction. Thus 6-bromoindole, commercially available from Biosynth Biochemica and Synthetica and protected on the ring nitrogen if necessary, can be coupled under palladium catalysis with 3-buten-1-ol using the procedures set forth in W. C. Frank et al., *J. Org. Chem.* 43: 2947 (1978) and N. J. Malek et al., *J. Org. Chem.* 47: 5395 (1982); the resulting alcohol intermediate allowed to react with p-toluenesulfonyl chloride to give the corresponding p-toluenesulfonate ester; and the ester treated with methylamine to give (E)-N-methyl-4-(6-indolyl)-3-buten-l-amine. The same compound can be produced by palladium catalyzed coupling of 6-bromoindole to N-methyl-N-(tert-butoxycarbonyl)-3-buten-1-amine (the synthesis of which is described above) and subsequently removing the tert-butoxycarbonyl protecting group. Alternatively, the 6-bromoindole can be reduced using diborane and trifluoroacetic acid in tetrahydrofuran as described by Gu et al., *Zhongguo Yaowu Huaxue Zazhi* 3: 58–9, 64 (1993) to give the corresponding 6-bromoindoline (6-bromo-2,3-dihydroindole), and the indoline protected as its tert-butoxycarbonyl derivative and used in the Heck coupling. Subsequent transformation as above and removal of the protecting group will yield (E)-N-methyl-4-(6-indolinyl)-3-buten-1-amine. Certain polycyclic phenols can also be converted into olefinic amines by first reacting them with trifluoromethanesulfonic anhydride to give the corresponding trifluoromethanesulfonate ester and subsequent palladium catalyzed coupling of the ester with a protected amine, as described by Sonesson et al., *J. Org. Chem.* 61: 4756 (1996), and further transformation as described above. Thus 8-hydroxyjulolidine, available from Aldrich Chemical Company, can be converted into (E)-N-methyl-4-(8-julolidinyl)-3-buten-1-amine.

Other polycyclic haloaromatics are available through well-known transformations of commercially available materials. Thus 1,3-benzodioxole (from Aldrich Chemical Company) can be nitrated to give 4-nitro-1,3-benzodioxole using the procedure described by Takakis et al., *J. Heterocycl. Chem.* 28: 625 (1991). Subsequent bromination, as taught by Dauksas et al., *Khim. Geterotsikl. Soedin.* Issue 9: 1183 (1979) gives 6-bromo-4-nitro-1,3-benzodioxole. Reduction of the nitro group to the amine group, accomplished with either tin or iron filings in hydrochloric acid, provides 4-amino-6-bromo-1,3-benzodioxole which can be coupled in a Heck process, as previously described, to give (E)-N-methyl-4-(6-(4-amino-l,3-benzodioxol)yl)-3-buten-1-amine.

In a similar application, 4-bromo-2-nitrophenol (available from Aldrich Chemical Company) and 4-bromo-2-nitroaniline (available from Trans World Chemicals, Inc.) can be reduced to 2-amino-4-bromophenol and 4-bromo-1,2-diaminobenzene respectively using tin and hydrochloric acid. Alternatively, stannous chloride can be used as the reducing agent, as described by Manjarrez et al., *Rev. Soc. Quim. Mex.* 30: 52 (1986). Reaction of 2-amino-4-bromophenol with trimethyl orthoformate in methanol provides 5-bromobenzoxazole, as reported by Kunz et al., *Org. Prep. Proced. Int.* 22: 613 (1990). Similarly, condensation of 4-bromo-1,2-diaminobenzene with formic acid in the presence of 6 M hydrochloric acid gives 5(6)-bromobenzimidazole, as described by Goldsmith et al. in U.S. Pat. No. 3,325,271. 5(6)-Bromobenzimidazole can also be made by brominating the commercially available benzimidazole (Aldrich Chemical Company) with bromine in aqueous ammonia according to Popov et al. in Soviet Union Patent No. 1,616,912. Applying the previously described Fleck chemistry to 5-bromobenzoxazole and 5(6)-bromobenzimidazole will produce (E)-N-methyl-4-(5-benzoxazolyl)-3-buten-1-amine and (E)-N-methyl-4-(5(6)-benzimidazolyl)-3-buten-1-amine, respectively. In another application of this chemistry, 4-bromo-1,2-diaminobenzene can be condensed with glyoxal hydrate to give 6-bromoquinoxaline, which can subsequently be converted into (E)-N-methyl-4-(6-quinoxalinyl)-3-buten-1-amine. In yet another application, 2-amino-4-bromophenol can be converted into 6-bromobenzoxazine by the action of 1,2-dihaloethane as described by Benoit et al., *J. Pharm. Chim.* 22:544 (1935). Thus produced, the 6-bromobenzoxazine can be protected as its N-tert-butoxycarbonyl derivative and submitted to Heck coupling and removal of the protecting group to give (E)-N-methyl-4-(6-benzoxazinyl)-3-buten-1-amine. Furthermore, acetylation of 4-bromo-1,2-diaminobenzene with acetic anhydride followed by treatment with thallium (III) trifluoroacetate in trifluoroacetic acid, as described by Lau et al., *Tetrahedron Lett.* 22:1175 (1981), gives 4-acetamido-6-bromo-2-methylbenzoxazole which can be converted into (E)-N-methyl-4-(6-(4-acetamido-2-methylbenzoxazol)yl)-3-buten-1-amine using the Heck coupling.

Certain 4-amino-6-halobenzofurans, which are starting materials for the Heck reaction, are readily accessible by elaboration of the previously described 3-halo-5-methoxyanilines, synthesized as described by Emokpae et al., *J. Chem. Soc., Perkin Trans.* 2(1): 14 (1977) and Liedholm, *Acta Chem. Scand., Ser. B,* 38: 877 (1984). Thus, 3-bromo-5-methoxyaniline can be demethylated with hydrobromic acid to give 3-amino-5-bromophenol. Protection of the amino group as its phthaloyl derivative and alkylation of the phenolic oxygen with allyl bromide and potassium carbonate will provide the allyl phenyl ether. This latter material (either as the free amine or the protected amine) can be induced to undergo Claisen rearrangement and ring closure to the corresponding 2,3-dihydro-2-methylbenzofuran by a variety of well established chemistries, such as that of Kim et al., *Hetrocycles* 36: 497 (1993) and those reviewed by Lutz, *Chem. Rev.* 84:205 (1984). The 4-amino-6-bromo-2,3-dihydro-2-methylbenzofuran, thus produced, can be converted into the target (E)-N-methyl-4-(6-(4-amino-2,3-dihydro-2-methylbenzofuran)yl)-3-buten-1 -amine by the palladium catalyzed coupling reactions and associated chemistry described earlier. This approach to the synthesis of benzofuran-containing alkenyl amines is general in the sense that a variety of allylic halides can be used to alkylate the phenol, thus producing, after Claisen rearrangement and ring closure, a variety of alkyl substituted 2,3-dihydrobenzofurans and 3,4-dihydrobenzopyrans.

Aryl substituted aliphatic amine compounds that possess a cyclopropyl moiety in the side chain can be prepared by a variety of methods. In one synthetic approach, aryl substituted cyclopropyl analogs can be prepared from the aforementioned aryl substituted olefinic amine compounds. Aryl substituted olefinic amine compounds possessing either an (E) or (Z) geometry can be converted to the corresponding trans and cis cyclopropane derivatives, respectively by treatment of the olefinic compounds with methylene iodide and a zinc-copper couple using the types of procedures set forth in H. E. Simmons et al., *J. Amer. Chem. Soc.* 81: 4256–4264 (1959). In particular, compounds such as (E)-4-(3-aminophenyl)-3-buten-1-amine, (E)-N-methyl-4-(3-aminophenyl)-3-buten-1-amine, (E)-N-methyl-5-(3-aminophenyl)-4-penten-2-amine, and (E)-N-methyl-5-(3-methoxyphenyl)-4-penten-2-amine can be converted to their corresponding cyclopropyl derivatives using the Simmons-Smith procedure.

Compounds of the present invention which possess an arylmethyl ether skeleton, such as an N-methyl-2-[(3-aminophenyl)methoxy]-ethan-1-amine type compound, can be prepared by a number of methods. In one approach, a 3-aminobenzyl alcohol type compound (N-protected as the phthalimide) can be condensed with the p-toluenesulfonate ester of ethanolamine, possessing a protected amine functionality, namely 2-p-toluenesulfonyloxy-[N-methyl-N-(tert-butoxycarbonyl)]-ethan-1-amine. Typically a strong base such as sodium hydride and an aprotic dipolar solvent such as N,N-dimethylformamide are used for the condensation. The tert-butoxycarbonyl protecting group of the resulting arylmethyl ether type compound can be removed with trifluoroacetic acid, followed by removal of the phthaloyl group with methylamine or hydrazine affording N-methyl-2-[(3-aminophenyl)methoxy]-ethan-1-amine. Substituted benzyl alcohol starting materials such as 3-aminobenzyl alcohol are commercially available from Aldrich Chemical Company. The phthalimide of 3-aminobenzyl alcohol can be prepared by heating 3-aminobenzyl alcohol with phthlic anhydride under reflux with azeotropic removal of water according to the method of J. F. Bunnett et al., *J. Org. Chem.* 27: 3836–3843 (1962). Protected amino side chain compounds such as 2-p-toluenesulfonyloxy-[N-methyl-N-(tert-butoxyearbonyl)]-ethan-1-amine can be prepared using the methods set forth in J. Christoffers, *Liebigs Ann./Recl.* (7): 1353–1358 (1997). By using this synthetic approach, substituted benzyl alcohol starting materials such as 4-methyl-3-nitrobenzyl alcohol, 4-chloro-3-nitrobenzyl alcohol, 3-nitrobenzyl alcohol, and 3,4-dimethoxybenzyl alcohol (commercially available from Acros Organics) can be elaborated to give N-methyl-2-[(4-methyl-3-nitrophenyl)methoxy]-ethan-1-amine, N-methyl-2-[(4-chloro-3-nitrophenyl)methoxy]-ethan-1-amine, N-methyl-2-[(3-nitrophenyl)methoxy]-ethan-1-amine, and N-methyl-2-[(3,4-dimethoxyphenyl)methoxy]-ethan-1-amine, respectively.

Compounds of the present invention with an arylmethyl ether functionality and which also possess a branched side chain, such as an N-methyl-1-[(3-aminophenyl)methoxy]-propan-2-amine type compound, can be prepared by a number of methods. In one approach, a 3-aminobenzyl alcohol type compound (N-proteeted as the phthalimide) can be alkylated with 1-bromo-2-propanol type compound containing an 0-protecting group, such as 2-(2-bromo-1-methylethoxy)tetrahydro-2H-pyran. Typically a strong base such as sodium hydride and a solvent such as N,N-dimethylformamide or tetrahydrofuran are used for the alkylation. The tetrahydropyranyl protecting group of the resulting arylmethyl ether type compound can be removed with aqueous sulfuric acid in methanol, affording 1-[(3-aminophenyl)methoxy]-propan-2-ol. The latter alcohol can be elaborated to the corresponding methylamino compound by conversion to its p-toluenesulfonate ester by treatment with p-toluenesulfonyl chloride, followed by tosylate displacement with methylamine and finally removal of the N-phthaloyl group affording N-methyl-1-[(3-aminophenyl)methoxy]-propan-2-amine. Side chain compounds such as 2-(2-bromo-1-methylethoxy)tetrahydro-2l1-pyran can be prepared from 1-bromo-2-propanol (commercially available from Aldrich Chemical Company) by treatment with 2,3-dihydropyran in dichloromethane with p-toluenesulfonic acid as a catalyst according to the methods of S. A. M. Nieuwenhuis et al., *Tetrahedron* 50: 13207–13230 (1994).

The manner in which optically active forms of arylmethoxy aliphatic amines, such as (2S)-N-methyl-1-[(3-aminophenyl)methoxy]-propan-2-amine type compounds, are provided can vary. In one approach, a 3-aminobenzyl alcohol type compound (N-protected as the phthalimide) can be alkylated with a chiral 1-bromo-2-propanol type compound containing an O-protecting group, such as (1S)-2-(2-bromo-1-methylethoxy)tetrahydro-2H-pyran using a base such as sodium hydride and a solvent such as N,N-dimethylformamide or tetrahydrofuran. The tetrahydropyranyl protecting group of the resulting chiral arylmethyl ether type compound can be removed with aqueous sulfuric acid in methanol, affording (2S)-1-[(3-aminophenyl)methoxy]-propan-2-ol. The resulting chiral alcohol intermediate can be converted to its corresponding tosylate, followed by tosylate displacement with methylamine with inversion of configuration, and finally removal of the N-phthaloyl group to give the chiral amine (2R)-N-methyl-1-[(3-aminophenyl) methoxy]-propan-2-amine. Chiral side chain compounds such as (1S)-2-(2-bromo-1-methylethoxy)tetrahydro-2H-pyran can be prepared from (2S)-1-bromo-2-propanol by treatment with 3,4-dihydro-2l1-pyran in dichloromethane with p-tolucnesulfonic acid as a catalyst according to the method of S. A. M. Nieuwenhuis et al., *Tetrahedron* 50: 13207–13230 (1994). The required (2S)-l-bromo-2-propanol can be obtained from (S)-propylene oxide (commercially available from Fluka) by treatment with hydrogen bromide in acetic acid at 0° C. The corresponding optical antipode, (2R)-N-methyl-1-[(3-aminophenyl) methoxy]-propan-2-amine can be prepared in an analogous manner from (R)-propylene oxide (commercially available from Fluka) by using the synthetic procedure of S. A. M. Nieuwenhuis et al. to prepare the tetrahydropyranyl ether of (2R)-1-bromo-2-propanol and by using the synthetic sequence described above.

Alternatively, the same chiral side-chain can be derived from N-methyl-L-alanine and N-methyl-l)-alanine (available from Sigma) by reduction with lithium aluminum hydride to give the corresponding N-methylaminopropanols, and subsequent reaction with di-tert-butyl dicarbonate (to protect the amino group) and p-toluenesulfonyl chloride (to esterify the alcohol). These transformations are similar to those reported by Schessinger et al., *Tetrahedron Lett.* 28: 2083–2086 (1987). The (S) and (R) 1-p-toluenesulfonyloxy-N-methyl-N-(tert-butoxycarbonyl)-2-propanamines which result can be used to alkylate phthaloyl protected 3-aminobenzyl alcohols in the same manner as described above for 2-p-toluenesulfonyloxy-N-methyl-N-(tert-butoxycarbonyl)-1-ethanamine.

Other 3-aminobenzyl alcohols are provided by well-known transformations of commercially available materials. Thus 3-aminoacetophenone, from Aldrich Chemical Company, can be reduced to racemic 3-amino-(x-methylbenzyl alcohol by sodium borohydride in the presence of acetic acid as described by Nieminen et al., *Tetrahedron Lett.* 28: 4725–8 (1987). Alternatively, the phthaloyl protected 3-aminoacetophenone can be reduced with either of the enantiomers of B-chlorodiisopino-campheylborane (DIP-chloride, Aldrich Chemical Company) to produce the protected, enantiomerically pure 3-amino-(α-methylbenzyl alcohol according to the procedures reported by Brown et al., Acc. Chem. Res. 25: 16 (1992). Other α-mono-substituted 3-aminobenzyl alcohols can be accessed by addition of the appropriate alkyl- or aryllithium or alkyl- or arylmagnesium halide reagent to the phthaloyl protected 3-aminobenzaldehyde, which can be made from commercially available 3-nitrobenzaldehyde (Aldrich Chemical Company). Thus, treatment of 3-nitrobenzaldehyde with ethylene glycol and p-toluenesulfonic acid produces the ethylene acetal. The nitro group can then be reduced with sodium borohydride to the amino group, which can be protected as its phthaloyl derivative. Hydrolysis of the ethylene acetal with aqueous acetic acid gives phthaloyl protected 3-aminobenzaldehyde. Addition of n-butyllithium to phthaloyl protected 3-aminobenzaldehyde yields the phthaloyl derivative of 1-(3-aminophenyl)-1-pentanol. Similarly di-substitution (methyl and alkyl or aryl) on the α-carbon of the benzyl alcohol can be accomplished by treatment of the phthaloyl protected 3-aminoacetophenone with alkyl- or aryllithium or alkyl- or arylmagnesium halide reagents. Alternatively, a variety of α-mono-substituted and α,α-di-substituted 3-aminobenzyl alcohols are available by the method of Guijarro et al., Tetirahectron 49: 469–82 (1993). Thus, 3-chloroaniline (Aldrich Chemical Company) is converted into its pivaloyl derivative and then treated sequentially with n-butyllithium, lithium metal in the presence of catalytic amount of naphthalene, and an aldehyde or ketone to produce the pivaloyl derivatives of ux-mono-substituted and α,α-di-substituted 3-aminobenzyl alcohols, respectively. Thus, when this process is carried out using cyclohexanone as the carbonyl component, the 1-(N-pivaloyl-3-aminophenyl)cyclohexanol is the product. In a similar process, reported by Gross et al., J. Org. Chem. 58: 2104–9 (1993), 3-bromoaniline is converted to its 3,3-(1,4-butanediyl)triazene derivative by diazotization and reaction with pyrrolidine. The 3-bromophenyltriazene can then be converted, by treatment with sec-butyllithium, into the 3-lithiophenyltriazene, which can then be reacted with carbonyl electrophiles to give triazene protected α-mono-substituted and α,α-di-substituted 3-aminobenzyl alcohols. Reaction of the protected (phthaloyl, pivaloyl, or triazene derivatives) 3-aminobenzyl alcohols (with or without α-substitution) with sodium hydride and either 2-p-toluenesulfonyloxy-1-(N-methyl-N-(tert-butoxycarbonyl)) ethanamine or $^1$-p-toluenesulfonyloxy-2-(N-methyl-N-(tert-butoxycarbonyl)propanamine (the synthesis of which is described above), will provide, after removal of the protecting groups, the corresponding N-methyl-2-(3-aminophenyl) methoxy-1-ethanamines and N-methyl-1-(3-aminophenyl) methoxy-2-propanamines with or without substitution a to the aniline ring. The amine protecting groups used in these ether syntheses can be removed by the following means: phthaloyl (hydrazine hydrate in methanol); pivaloyl (lithium aluminum hydride); 3,3-(1,4-butanediyl)triazene (nickel-aluminum alloy in methanolic potassium hydroxide); tert-butoxycarbonyl (trifluoroacetic acid). Thus, the reaction of phthaloyl protected 3-amino-u,-methylbenzyl alcohol with sodium hydride and 1-p-toluenesulfonyloxy-2-(N-methyl-N-(tert-butoxycarbonyl))propanamine, and subsequent treatment with hydrazine hydrate (to remove the phthaloyl group) and then trifluoroacetic acid (to remove the tert-butoxycarbonyl group), will provide N-methyl-1-(1-(3-aminophenyl)ethoxy)-2-propanamine. Either enantiomer of either component may be used or the racemate of one component can be condensed with a single enantiomer of the other to give diasteriomeric amines, which are potentially separable by chromatographic methods. In another application of this chemistry, the triazene derivative of 1-(3-aminophenyl)cyclohexanol can be reacted with sodium hydride and 2-p-toluenesulfonyloxy-1-(N-methyl-N-(tert-butoxycarbonyl)ethanamine, and subsequently treated with nickel-aluminum alloy in methanolic potassium hydroxide (to convert the triazene to the amino group) and then trifluoroacetic acid, producing N-methyl-2-(1-(3-aminophenyl)cyclohexyloxy)-1-ethanamine.

Aromatic ring-substituted 3-aminobenzyl alcohols can also be used to produce compounds of the present invention. The means by which such ring-substituted 3-aminobenzyl alcohols are produced can vary. One method consists of reacting a substituted N-protected 3-haloaniline with n-butyllithium or sec-butyllithium followed by a formaldehyde equivalent (like paraformaldehyde), as described by Guijarro et al., Tetrahedron 49: 469–82 (1993) and Gross et al., J. Org. Chem. 58: 2104–9 (1993). Using this technology, the various ring-substituted bromoanilines and fused ring aryl bromides described earlier (as useful in the Heck coupling) are potential starting materials for production of the corresponding benzyl alcohols. Thus, 3-bromo-5-methoxyaniline (synthesized as described by Emokpae et al., J. Chem. Soc., Perkin Trans. 2(1): 14–17 (1977)) can be converted into its triazene derivative, lithiated, and reacted with paraformaldehyde (as described by Gross et al., J. Org. Chem. 58: 2104–9 (1993)). The resulting triazene protected 3-amino-5-methoxybenzyl alcohol can be reacted with sodium hydride and 2-p-toluenesulfonyloxy-N-methyl-N-(tert-butoxycarbonyl)-1-ethanamine. Removal of the protecting groups (as previously described) then affords N-methyl-2-(3-amino-5-methoxyphenyl)methoxy-1-ethanamine.

Certain other ring-substituted and fused-ring benzyl alcohols are readily prepared from the corresponding aldehydes and carboxylic acids by reduction with a hydride reducing agent. For example, M. Bianchi et al., Chim. Intl. 49: 392 (1967) described the conversion of 3-amino-4-hydroxybenzoic acid (Aldrich Chemical Company) into its formamide by refluxing formic acid and the subsequent heating of the formamide to produce 5-benzoxazolecarboxylic acid. Treatment of the acid with thionyl chloride produces the corresponding acid chloride which can then be reduced to 5-(hydroxymethyl) benzoxazole. This fused-ring benzyl alcohol can be condensed with 1-p-toluenesulfonyloxy-N-methyl-N-(tert-butoxycarbonyl)-2-propanamine using sodium hydride to give, after deprotection, N-methyl-1-(5-benzoxazolyl) methoxy-2-propanamine. In another similar case, piperonylic acid (Aldrich Chemical Company) can be nitrated to give 5-nitropiperonylic acid (5-nitro-3,4-methylenedioxybenzoic acid), which can subsequently be reduced to 5-aminopiperonyl alcohol (5-amino-3,4-methylenedioxybenzyl alcohol) by sequential treatment with tin in hydrochloric acid and lithium aluminum hydride. Protection of this amine as its phthaloyl derivative, followed by reaction with sodium hydride and 2-p-toluenesulfonyloxy-N-methyl-N-(tert-butoxycarbonyl)-1-ethanamine results in formation of the benzyl ether compound. Subsequent removal of the protecting groups, affords N-methyl-2-(5-amino-3,4-methylenedioxyphenyl)methoxy-1-ethanamine.

Compounds of the present invention which possess an arylmethyl ether functionality with a cyclic amine fragment, such as a 3-((2-pyrrolidinylethoxy)methyl)phenylamine type compound can be prepared by a variety of methods. By one synthetic approach, the p-toluenesulfonate ester of a 3-aminobenzyl alcohol type compound (N-protected as the phthalimide) can be used to alkylate 1-(2-hydroxyethyl) pyrrolidine (commercially available from Aldrich Chemical Company) in the presence of a base such as sodium hydride in a solvent such as tetrahydrofuran or N,N-dimethylformamide. The phthaloyl protecting group of the resulting intermediate can be removed by treatment with methylamine or hydrazine yielding the 3-((2-pyrrolidinylethoxy)methyl)phenylamine.

Compounds of the present invention which possess an arylmethyl ether functionality with a chiral azacyclic fragment, such as 3-((pyrrolidin-2(S)-ylmethoxy)methyl) phenylamine and 3-(((1-methylpyrrolidin-2(S)-yl)methoxy) methyl)phenylamine type compounds can be prepared by a number of methods. By one synthetic approach, the p-toluenesulfonate ester of a 3-aminobenzyl alcohol type compound (N-protected as the phthalimide) can be used to alkylate (S)-1-(tert-butoxycarbonyl)-2-pyrrolidinemethanol in the presence of a base such as sodium hydride in a solvent such as tetrahydrofuran or N,N-dimethylformamide. The tert-butoxycarbonyl group can be removed with strong acid such as trifluoroacetic acid or hydrochloric acid and the phthaloyl group can be removed by treatment with hydrazine or methylamine producing 3-((pyrrolidin-2(S)-ylmethoxy)methyl)phenylamine. The required (S)-1-(tert-butoxycarbonyl)-2-pyrrolidinemethanol is commercially available from Aldrich Chemical Company. The corresponding enantiomer, 3-((pyrrolidin-2(R)-ylmethoxy)methyl) phenylamine can be prepared in an analogous manner from (R)-1-(tert-butoxycarbonyl)-2-pyrrolidinemethanol (commercially available from Aldrich Chemical Company). It should be mentioned that (S)-1-(tert-butoxycarbonyl)-2-pyrrolidinemethanol and (R)-1-(tert-butoxycarbonyl)-2-pyrrolidinemethanol can be prepared according to the methods of D. A. Evans et al., *J. Am. Chem. Soc.* 101: 371–378 (1979) and B. D. Harris et al., *Heterocycles* 24: 1045–1060 (1986) starting from commercially available (Aldrich Chemical Company) D-proline and L-proline. Compounds of the present invention such as 3-(((1-methylpyrrolidin-2 (S)-yl)methoxy)methyl)phenylamine can be prepared in a similar manner by the alkylation of (S)-1-methyl-2-pyrrolidinemethanol (available from Aldrich Chemical Company) with the previously mentioned p-toluenesulfonate ester of a 3-aminobenzyl alcohol (N-protected as the phthalimide), followed by removal of the tert-butoxycarbonyl and phthaloyl protecting groups. The corresponding enatiomer of the above N-methyl compound, namely 3-(((1-methylpyrrolidin-2(R)-yl) methoxy)methyl)phenylamine can be prepared in a similar manner by the alkylation of (R)-1-methyl-2-pyrrolidinemethanol with the previously mentioned p-toluenesulfonate ester of a 3-aminobenzyl alcohol (N-protected as the phthalimide), followed by removal of the tert-butoxycarbonyl and phthaloyl protecting groups. The required (R)-1-methyl-2-pyrrolidinemethanol can be prepared by the method of R. E. Gawley et al., *J. Org. Chem.* 60 (18): 5763–5769 (1995).

Compounds of the present invention which possess an arylmethyl ether functionality with a chiral azacyclic fragment, such as 3-((2(S)-azetidinylmethoxy)methyl) phenylamine and 3-(((1-methyl-2(S)-azetidinyl)-methoxy) methyl)phenylamine type compounds can be prepared by a variety of synthetic methods. In one synthetic approach, the p-toluenesulfonate ester of a 3-aminobenzyl alcohol type compound (N-protected as the phthalimide) can be used to alkylate (S)-1-(tert-butoxycarbonyl)-2- azetidinemethanol in the presence of a base such as sodium hydride in a solvent such as tetrahydrofuran or N,N-dimethylformamide. The tert-butoxycarbonyl group can be removed with a strong acid such as trifluoroacetic acid or hydrochloric acid and the phthaloyl group can be removed by treatment with hydrazine or methylamine affording 3-((2(S)-azetidinylmethoxy) methyl)phenylamine. The requisite nonracernic compound, (S)-1-tert-butoxycarbonyl)-2-azetidinemethanol can be prepared from (S)-2-azetidinecarboxylic acid (commercially available from Aldrich Chemical Company) using the method of M. A. Abreo et al., *J. Med. Chem.* 39: 817–825 (1996). The enantiomeric azetidinyl compound, 3-((2(R)-azetidinylmethoxy)-methyl)phenylamine can be prepared in an analogous way by coupling 3-aminobenzyl alcohol type compound (N-protected as the phthalimide) with (R)-1-(benzyloxycarbonyl)-2-azetidinemethanol, followed by treatment with base, such as methanolic potassium hydroxide to remove the benzyloxycarbonyl protecting group and treatment with hydrazine or methylamine to remove the phthaloyl protecting group. The required (R)-1-(benzyloxycarbonyl)-2-azetidinemethanol can be prepared from D-methionine using the methodology of M. A. Abreo et al., *J. Med. Chem.* 39: 817–825 (1996). Compounds of the present invention such as 3-(((1-methyl-2(S)-azetidinyl) methoxy)methyl)phenylamine and its enantiomeric compound, 3-(((1-methyl-2(R)-azetidinyl)methoxy)methyl) phenylamine can be prepared by methylation of the previously described secondary amino compounds, 3-((2(S)-azetidinylmethoxy)methyl)phenylamine and 3-((2(R)-azetidinylmethoxy)methyl)phenylamine, respectively, each N-protected as the phthalimide. Methylation methods employing aqueous formaldehyde and sodium cyanoborohydride as described by M. A. Abreo et al., *J. Med. Chem.* 39: 817–825 (1996) can be used. Removal of the phthaloyl group can be accomplished under mild conditions usning sodium borohydride in 2-propanol as described by J. O. Osby et al., *Tetrahedon Lett.* 25(20): 2093–2096 (1984).

Using this approach, other compounds containing arylmethyl ether and azacyclic functionality can be made. Thus, the commercially available 3-pyrrolidinol and 3-quinuclidinol (both from Aldrich Chemical Company) can be converted into their N-tert-butoxycarbonyl derivatives by reaction with di-tert-butyl dicarbonate. Subsequent alkylation with sodium hydride and the p-toluenesulfonate ester of phthaloyl protected 3-aminobenzyl alcohol in N,N-dimethylformamide, followed by removal of the protecting groups, will generate 3-(3-aminobenzyloxy)pyrrolidine and 3-(3-aminobenzyloxy)quinuclidine, respectively. Alternatively, the alkylation can be carried out with 3-nitrobenzyl bromide (Aldrich Chemical Company) to produce the corresponding 3-(3-nitrobenzyloxy)pyrrolidine and 3-(3-nitrobenzyloxy)quinuclidine.

Compounds of the present invention may contain a thiazoline ring. The methods by which such thiazoline containing compounds can be synthesized can vary. One method involves the condensation of a thioamide or thiourea with an α-haloaldehyde, such as 2-chloroacetaldehyde or 2-bromoacetaldehyde. The requisite thioamides and thioureas can be produced in a number of ways. For instance, the alkoxide of 3-nitrobenzyl alcohol (Aldrich Chemical Company) can be converted to 3-chloro-1-((3-nitrophenyl) methoxy)propane by treatment with 3-chloro-1-iodopropane (Aldrich Chemical Company). Conversion of this compound to the corresponding amine can be accomplished by a variety of methods known in the art, such as by Gabriel synthesis (Gibson and Bradshaw, *Agnew. Chem. Int. Eng. Ed.* 7: 919 (1968)), whereby the alkyl chloride is converted to the phthalimide followed by removal of the phthaloyl protecting group with hydrazine. Then, the resulting 3-((3-nitrophenyl)methoxy)-1-propanamine can be converted into its thiourea by treatment with thiocyanic acid in DMF. This mono-substituted thiourea can then be cyclized to form N-(2-thiazolyl)-3-((3-nitrophenyl)methoxy)-1-propanamine using chloracetaldehyde (Aldrich Chemical Company) in the presence of magnesium sulfate as described by Bramley et al., *J. Chem. Soc. Perkin Trans. I* 3: 639 (1987). Finally, any number of methods known to the art of organic synthesis can be used to reduce the aryl nitro group to give the desired aryl amine, N-(2-thiazolyl)-3-((3-aminophenyl)methoxy)-1-propanamine. One such method is the use of hexarubidium-carbonyl and N,N,N-tetramethyl-1,3-propanediamine according to the method of Kiyotomi et al., *J. Mol. Catal.* 88: L267 (1994). Alternatively, the thiourea of 3-((3-nitrophenyl)methoxy)-1-propanamine can be cyclized to form 3-(3-((3-nitrophenyl)methoxy)propyl)-2,3-dihydrothiazolin-2-imine, using chloroacetaldehyde in the presence of hydrochloric acid as described by Bramley et al., *J. Chem. Soc. Perkin Trans. I* 3: 639 (1987). Reduction to the corresponding aryl amine can be accomplished as described above.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. Nos. 5,597,919 to Dull et al., 5,616,716 to Dull et al. and 5.663,356 to Ruecroft et al.

Compounds of the present invention exhibit activity at acetylcholine receptors, are useful towards modulating release of ligands involved in neurotransmission. Compounds of the present invention are selective to certain nicotinic acetylcholine receptor subtypes, and can act as agonists at those receptor subtypes. Compounds of the present invention are useful for treating those types of conditions and disorders for which other types of nicotinic compounds have been proposed as therapeutics. See, for example, those types of conditions and disorders set forth in Williams et al. *DN&P* 7(4):205–227 (1994), Arneric et al., *CNS Drug Rev.* 1(1):1–26 (1995), Arneric et al., *Exp. Opin. Invest. Drugs* 5(1): 79–100 (1996), Bencherif et al., *JPET* 279:1413–1421 (1996), Lippiello et al., *JPET* 279:1422–1429 (1996), Damaj et al., *Neuroscience* (1997), flolladay et al., *J. Med. Chern* 40(28): 4169–4194 (1997), Bannon et al., *Science* 279: 77–80 (1998), PCT WO 94/08992, PCT WO 96/31475, PCT WO 97/19059, European Patent Application 857,725, and U.S. Pat. Nos. 5,278,176 to Lin, 5,583,140 to Bencherif et al., 5,597,919 to Dull et al., 5,604,231 to Smith et al., 5,616,716 to Dull et al. and 5,811,442 to Bencherif et al. the disclosures of which are incorporated herein by reference in their entireties. Compounds of the present invention can be used to treat presenile dementia (early onset Alzheimer's disease), senile dementia (dementia of the Alzheimer's type), Parkinsonism including Parkinson's disease, anxiolysis, attention deficit hyperactivity disorder, depression, dyslexia, epilepsy, Huntington's chorea, hyperkinesia, mania, neuro-endocrine disorders, schizophrenia, sleep disorders, tardive dyskinesia, Tourette's syndrome, autism, and dysregulation of food intake (e.g., bulimia and anorexia). Compounds of the present invention can be used as anti-infectious agents (e.g., to treat bacterial and viral infections), anti-inflammatory agents (e.g., to treat acute cholangitis, aphteous stomatitis, and ulcerative colitis), anti-neoplastic agents, inhibitors of cytokines release (e.g., to treat symptoms associated with cachexia, inflammation, neurodegenerative diseases, viral infection and neoplasia), modifiers of the vasculature tone (e.g., as occurs in stroke patients), and as agents to treat conditions associated with microcirculation (e.g., to treat symptoms associated with Raynaud's disease and Raynaud syndrome). Compounds of the present invention can be used as analgesics, in treating substance abuse withdrawal and in substitution therapies, in treating inflammatory bowel disease, in treating cardiovascular disfunction, as depolarizing muscle relaxants, and as probes for neuro-imaging and in the life sciences.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that affect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. Nos. 5,604,231 to Smith et al. and 5,811,442 to Bencherif et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 5 mg/kg of patient weight. Often, the compounds of the present invention are administered in an amount from 1 mg to less than 100 ug/kg of patient weight, frequently between about 1 ug to less than 100 ug/kg of patient weight, and preferably between about 1 ug to about 50 ug/kg of patient weight. For compounds of the present invention that do not induce effects on muscle type nicotinic receptors at low concentrations, the effective dose is less than 5 mg/kg of patient weight; and often such compounds are administered in an amount from 1 ug to less than 5 mg/kg of patient weight. The foregoing effective doses typically represent that amount administered as a single dose, or as one or more doses administered over a 24 hour period.

For human patients, the effective dose of typical compounds generally requires administering the compound in an amount of at least about 0.1, often at least about 10, and frequently at least about 25 ug/ 24 hr./ patient. For human patients, the effective dose of typical compounds requires administering the compound which generally does not exceed about 500, often does not exceed about 400, and frequently does not exceed about 300 ug/ 24 hr./ patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1. The log P values of such typical compounds generally are less than about 3.5, often are less than about 3, and sometimes are less than about 2.5. Log P values provide a measure of the ability of a compound to pass across a diffusion barrier, such as a biological membrane. See, Hansch. et al., *J. Med. Chem.* 11:1 (1968).

The compounds useful according to the method of the present invention have the ability to bind to, and in most circumstances, cause activation of, nicotinic cholinergic receptors of the brain of the patient (e.g., such as those receptors that modulate dopamine release). As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 uM, often are less than about 100 nM, and frequently are less than about 50 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively neurotransmitter secretion from, nerve ending preparations (e.g., striatal synaptosomes). As such, such compounds have the ability to cause relevant neurons to become activated, and to release or secrete dopamine or other neurotransmitters. Generally, typical compounds useful in carrying out the present invention are potent in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 uM). Generally, typical preferred compounds useful in carrying the present invention activate isotopic rubidium ion flux by less than 15 percent, often by less than 5 percent, of that maximally provided by S(−) nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionictype nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical preferred compounds useful in carrying out the present invention activate isotopic rubidium ion flux by less than 15 percent, often by less than 5 percent, of that maximally provided by S(−) nicotine.

Compounds of the present invention, when employed in effective amounts in accordance with the method of the present invention, are effective towards providing some degree of prevention of the progression of CNS disorders, amelioration of the symptoms of CNS disorders. and amelioration to some degree of the recurrence of CNS disorders. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less ⅓, frequently less than ⅕, and often less than ⅒, that amount sufficient to cause any side effects to a significant degree.

The following examples are provided to illustrate the present invention, and should not be construed as limiting thereof.

EXAMPLE 1
Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., *Biochem, Pharmacol.* 22:3099 (1973).

EXAMPLE 2
Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine on a percentage basis.

EXAMPLE 3
Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

EXAMPLE 4
Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

EXAMPLE 5
Determination of Log P Value

Log P values, which have been used to assess the relative abilities of compounds to pass across the blood-brain barrier (Hansch, et al., *J. Med. Chem.* ii:1 (1968)), were calculated using the Cerius$^2$ software package Version 3.5 by Molecular Simulations, Inc.

EXAMPLE 6

Sample No. 1 is (E)-4-(3-aminophenyl)-3-buten-1-amine, which was prepared in accordance with the following techniques:
N-3-(Butenyl)phthalimide
N-3-(butenyl)phthalimide was prepared as a white, crystalline powder, mp 52–52.5° C. in 92.9% using the procedure of Frank et al., *J. Org. Chem.* 43:2947 (1978).
(E)-N- [4-(3-Aminophenyl)-3-butenyl]phthalimide
Under a nitrogen atmosphere, a mixture of N-3-(butenyl) phthalimide (4.22 g, 21.0 mmol), 3-bromoaniline (3.50 g, 20.4 mmol, Aldrich Chemical Company), palladium(II) acetate (46.0 mg, 0.20 mmol), tri-o-tolylphosphine (248 mg, 0.81 mmol), triethylamine (5.81 g, 57.4 mmol), and acetonitrile (8 mL) was stirred and heated at 130° C. for 21 h. Upon cooling to ambient temperature, the solids were partitioned between water (100 mL) and $CH_2Cl_2$ (100 mL). The aqueous phase was separated and extracted with $CH_2Cl_2$ (75 mL). The combined $CH_2Cl_2$ extracts were washed with water (70 mL), filtered through Celite® filter aid (8 g), washing the filter cake with $CH_2Cl_2$ (25 ml,). The filtrate was dried ($Na_2SO_4$), filtered, and concentrated on a rotary evaporator. The resulting residue was vacuum dried at 45° C. for 18 h to give 6.36 g of a light-yellow, lumpy powder. The product was recrystallized from $CH_2Cl_2$-2-propanol, filtered, washed with cold 2-propanol (2×10 mL) and vacuum dried at 50° C. for 2 h to give 5.00 g (84.0%) of a light-yellow powder. TLC analysis on silica gel, eluting with $CHCl_3$-methanol (98:2, v/v) indicated the presence of impurities. Consequently, the product was recrystallized from DMF-water, filtered, washed with cold 2-propanol (3×2 mL), and vacuum dried at 50° C. for 18 h to give 4.64 g (78.0%) of a yellow powder, mp 159–162° C. An analytical sample was recrystallized from ethyl acetate-hexane (1:2, v/v) affording a light-beige powder, mp 159–162° C., $R_f$ 0.41 in ethyl acetate-hexane (1:1, v/v).

(E)-4-(3-Aminophenyl)-3-buten-1-amine

A mixture of (E)-N-[4-(3-aminophenyl)-3-butenyl] phthalimide (3.50 g, 12.0 mmol) in ethanol (50 mL) was treated with 50 g of a 25% (w/w) solution of methylamine in ethanol. The resulting yellow solution was stirred at room temperature for 3 h and concentrated on a rotary evaporator. The product was vacuum dried at 50° C. for 1 h to give 4.26 g of a viscous, orange-yellow oil. The oil was purified by column chromatography on silica gel (200 g), eluting with methanol-concentrated ammonium hydroxide (10:1, v/v). Based upon TLC analysis, selected fractions were combined and concentrated on a rotary evaporator. The product was purified by vacuum distillation (bulb to bulb) to give 124 mg (6.4%) of a colorless oil, bp 105–110° C. at 0.075 mm Hg. Purification of a second fraction by vacuum distillation produced an additional 141 mg of a colorless oil, bp 104–105° C. at 0.075 mm Hg, bringing the total yield to 249 mg (12.8%).

Sample No. 1 exhibits a log P of 1.04, and such a favorable log P value indicates that the compound has the capability of passing the blood-brain barrier. The compound exhibits a Ki of 542 nM. The binding constant indicates that the compound exhibits high affinity binding to certain CNS nicotinic receptors.

Sample No. 1 exhibits an $EC_{50}$ value of 12600 nM and an $E_{max}$ value of 74% for dopamine release, indicating that the compound induces neurotransmitter release thereby exhibiting known nicotinic pharmacology.

Sample No. 1 exhibits an $E_{max}$ of 0% (at a concentration of 100 uM) at muscle-type receptors, indicating that the compound does not induce activation of muscle-type receptors. The sample exhibits an Emax of 4% (at a concentration of 100 uM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree.

EXAMPLE 7

Sample No. 2 is (E)-N-methyl-4-(3-aminophenyl)-3-buten-1-amine, which was prepared in accordance with the following techniques:

N-Methyl-3-buten-1-amine

Under a nitrogen atmosphere, anhydrous DMF (40 mL) was added via syringe to methylamine (40 mL, 43.2 g, 1.4 mol, condensed from the gas phase) at −78° C. Anhydrous potassium carbonate (19.36 g, 140 mmol) was added to the stirring solution, followed by 4-bromo-1-butene (18.9 g, 140 mmol, Aldrich Chemical Company). The resulting mixture was allowed to slowly warm to ambient temperature over 16 h. The mixture was poured into water (150 ml,) and extracted with ether (8×50 mL). The combined ether extracts were dried ($Na_2SO_4$), filtered, and distilled at atmospheric pressure to give 6.86 g (57.6%) of a colorless oil, bp 80–82° C.

N-Methyl-N-(3-buten-1-yl)benzamide

Under a nitrogen atmosphere, a solution of N-methyl-3-buten-1-amine (6.86 g, 80.6 mmol) in dichloromethane (100 mL) was cooled to 0° C., and triethylamine (17.93 g, 177.2 mmol) and 4-(N,N-dimethylamino)pyridine (207 mg) were added. A solution of benzoyl chloride (11.89 g, 84.6 mmol) in dichloromethane (60 mL) was added dropwise via addition funnel over 1 h at 0–5° C. The resulting turbid mixture was stirred 3 h at 0° C. The mixture was then washed in succession with 1 M HCl solution (3×75 mL), 5% $NaHCO_3$ solution (3×100 mL), and water (100 mL). The organic phase was dried ($Na_2SO_4$), filtered, and concentrated on a rotary evaporator to a yellow oil (12.66 g). Vacuum distillation using a 6 in. Vigreaux column and a short path distillation apparatus afforded 8.58 g (56.3%) of a colorless oil, bp 100–103° C. at 0.1 mm Hg.

(E)-N-Methyl-N-[4-(3-aminophenyl)-3-buten-1-yl]benzamide

Under a nitrogen atmosphere, a mixture of N-methyl-N-(3-buten-1 -yl)benzamide (2.15 g, 11.36 mmol), 3-iodoaniline (2.49 g, 11.36 mmol, Aldrich Chemical Company), palladium(II) acetate (25.5 mg, 0.11 mmol), and triethylamine (2.30 g, 22.70 mmol) was stirred and heated under reflux at 105–110° C. (oil bath temperature) for 52 h. The dark-brown solution was allowed to cool to ambient temperature and was diluted with water (20 ml,) and $CHCl_3$ (40 mL). The water layer was separated and extracted with $CHCl_3$ (2×10 mL). The combined $CHCl_3$ extracts were washed with saturated NaCl solution (10 mL), dried ($CHCl_3$), filtered, and concentrated by rotary evaporation. Further drying under high vacuum (0.3 mm Hg) for 15 h produced a viscous, brown oil (3.59 g). The crude material was purified by column chromatography on silica gel (155.5 g, 4.0 cm i.d.×60.5 cm column) eluting with EtOAc (25→67%, v/v) in $CHCl_3$. Fractions containing the product ($R_f$ 0.34 in EtOAc—$CHCl_3$, 1:1, v/v) were combined, concentrated by rotary evaporation, and vacuum dried at 45° C. for 15 h to give 1.60 g (50.2%) of an amber oil.

(E)-N-Methyl-4-(3-aminophenyl)-3-buten-1-amine

A solution of (E)-N-methyl-N-[4-(3-aminophenyl)-3-buten-1-yl]benzamide (1.52 g, 5.42 mmol) in 6 M HCl solution (55 mL) was stirred and heated under reflux at 105° C. (oil bath temperature) for 17.5 h. The resulting dark-brown solution was allowed to cool to ambient temperature and was further cooled to 0° C. A 20% NaOH solution (85 mL) was carefully added with stirring giving pH 13. The resulting mixture was extracted with $CHCl_3$ (3×50 mL). The combined tan $CHCl_3$ extracts were washed with saturated NaCl solution (50 mL), dried ($Na_2SO_4$), filtered, and concentrated by rotary evaporation. Further drying at 0.6 mm Hg for 3 h gave a thick, light-brown oil (1.18 g). TLC analysis ($CH_3OH$—$Et_3N$, 97.5:2.5, v/v) indicated the presence of (E)-N-methyl-N-(4-(3-aminophenyl)-3-buten-1-yl) benzamide ($R_f$ 0.60) along with the desired product ($R_f$ 0. 19). Consequently, the crude oil was treated with concentrated HCl (75 mL) and stirred and heated under reflux for 16 h. The mixture was cooled to 0° C., basified with 20% NaOH solution (50 ml,) to pH 12, and extracted with $CHCl_3$ (4×50 ml,). The combined $CHCl_3$ extracts were washed with saturated NaCl solution (50 mL), dried ($Na_2SO_4$), filtered, and concentrated by rotary evaporation. Further drying under high vacuum produced a brown oil (888 mg). TLC analysis again indicated the presence of (E)-N-methyl-N-[4-(3-aminophenyl)-3-buten-1-yl]benzamide. Consequently, the crude material was treated with 20% sulfuric acid solution (50 mL) and stirred and heated under reflux at 135° C. (oil bath temperature) for 6 h. The resulting mixture was cooled to ambient temperature and was further cooled to 0° C. A 20% NaOH solution (40 ml,) was carefully added, with stirring, giving pH 12. The resulting mixture was extracted with $CHCl_3$ (5×40 mL). The combined $CHCl_3$ extracts were washed with saturated NaCl solution (50 mL), dried ($Na_2SO_4$), filtered, and concentrated by rotary evaporation. Further drying under high vacuum produced a dark-brown syrup (734 mg). The crude product was purified by column chromatography on silica gel (50 g, 2.0 cm i.d. column) eluting with $CH_3OH$—$Et_3N$ (97.5:2.5, v/v). Selected fractions containing the product were combined and concentrated by rotary evaporation. The residue was dissolved in $CHCl_3$, dried ($Na_2SO_4$), filtered, concentrated by rotary evaporation, and further dried under high vacuum to give 241.3 mg (25.2%) of a light-brown oil. A portion (169.8 mg) of this material was further purified by column chromatography on silica gel (25 g, 2.0 cm i.d. column) eluting with $CH_3OH$-$Et_3N$ (97:3, v/v). Selected fractions containing the product ($R_f$ 0.24 in $CH_3OH$—$Et_3N$ (97:3, v/v)) were combined and concentrated by rotary evaporation. The resulting yellow oil was dissolved in $CHCl_3$, dried ($Na_2SO_4$), filtered, concentrated by rotary evaporation, and further dried at 0.5 mm Hg for 3 h to give 130.6 mg of a viscous, reddish brown oil.

Sample No. 2 exhibits a log P of 1.66, and such a favorable log P value indicates that the compound has the capability of passing the blood-brain barrier. The compound exhibits a Ki of 42 nM, indicating that the compound exhibits good binding to certain CNS nicotinic receptors.

Sample No. 2 exhibits an $EC_{50}$ value of 913 nM and an $E_{max}$ value of 78% for dopamine release, indicating that the compound induces neurotransmitter release thereby exhibiting known nicotinic pharmacology.

Sample No. 2 exhibits an $E_{max}$ of 7% (at a concentration of 100 uM) at muscle-type receptors, indicating that the compound does not induce activation of muscle-type receptors to any significant degree. Sample No. 2 exhibits an $E_{max}$ of 3% (at a concentration of 100 uM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle and ganglion effects to any significant degree.

EXAMPLE 8

Sample No. 3 is (E)-N-methyl-5-(3-aminophenyl)-4-penten-2-amine, which was prepared in accordance with the following techniques:

N-(3-Bromophenyl)phthalimide

A stirring slurry of 3-bromoaniline (3.00 g, 17.44 mmol), phthalic anhydride (2.58 g, 17.44 mmol), and toluene (45 ml) was heated under reflux, using a Dean-Stark apparatus, at 140° C. (oil bath temperature) for 24 h. After cooling to ambient temperature, the solution was concentrated by rotary evaporation. The resulting off-white solid was purified by column chromatography on silica gel (150 g, Merck 70–230 mesh) eluting with $CHCl_3$-acetone (9:1, v/v) to collect unreacted 3-bromoaniline ($R_f$ 0.61) and phthalic anhydride ($R_f$ 0.43). Elution with $CHCl_3$-methanol (9:1, v/v) gave the product ($R_f$ 0.38). Selected fractions containing the product were combined and concentrated by rotary evaporation to give 1.53 g of an off-white to light-beige solid. Impure fractions were combined and concentrated by rotary evaporation. The resulting white solid was dissolved in a mixture of $CHCl_3$, acetone, and methanol and re-chromatographed on silica gel (150 g). Elution with CHCl3 removed impurities; the product was then eluted with $CHCl_3$-acetone (4:1, v/v). Selected fractions were combined, concentrated by rotary evaporation, and vacuum dried for 16 h to give 1.41 g of an off-white to light-beige solid, mp 176–179° C., bringing the total yield to 2.94 g (55.8%).

4-Penten-2-ol p-Toluenesulfonate

Under a nitrogen atmosphere, p-toluenesulfonyl chloride (16.92 g, 88.75 mmol) was added to a cold (2° C.), stirring solution of 4-penten-2-ol (7.28 g, 84.52 mmol, Aldrich Chemical Company) in pyridine (60 mL). The solution was stirred at 2–5° C. for 2 h and allowed to warm to ambient temperature over several hours. The mixture, containing white solids, was poured into cold 3 M HCl solution (250 mL) and extracted with $CHCl_3$ (4×75 mL). The combined $CHCl_3$ extracts were washed with 3 M HCl solution (4×100 mL), saturated NaCl solution (2×50 mL), dried ($Na_2SO_4$), filtered, concentrated on a rotary evaporator, and further dried under high vacuum to afford 17.38 g (85.6%) of a light-amber oil.

N-Methyl-4-penten-2-amine

A 180-mL thick-walled glass pressure tube was charged with 4-penten-2-ol p-toluenesulfonate (17.30 g, 71.99 mmol) followed by a 40% solution of aqueous methylamine (111.85 g, 1.44 mol). The tube was sealed, and the mixture was stirred and heated at 122° C. for 16 h and allowed to cool to ambient temperature. After further cooling to 0–5° C., the light-yellow solution was saturated with solid NaCl and extracted with diethyl ether (6×40 mL, inhibitor-free). The combined light-yellow ether extracts were dried ($Na_2SO_4$) and filtered. The ether was removed by distillation at atmospheric pressure using a 6-inch Vigreaux column and a short-path distillation apparatus. The residual light-yellow oil was distilled at atmospheric pressure collecting 3.72 g (52.1 %) of a colorless oil, bp 75–105° C.

N-Methyl-N-(tert-butoxycarbonyl)-4-penten-2-amine

Di-tert-butyl dicarbonate (6.84 g, 31.35 mmol) was quickly added in several portions to a cold (0–5° C.), stirring solution of N-methyl-4-penten-2-amine (3.66 g, 25.68 mmol) in dry tetrahydrofuran (25 mL, freshly distilled from sodium and benzophenone). The resulting light-yellow solution was stirred and allowed to warm to ambient temperature over several hours. The solution was concentrated on a rotary evaporator. The resulting oil was vacuum distilled using a short-path distillation apparatus, collecting 5.22 g (88.4%) of an almost colorless oil, bp 85–86° C. at 5.5 mm Hg.

(E)-N-Methyl-N-(tert-butoxycarbonyl)-5-[(1-N-phthaloyl)-3-phenyl]-4-penten-2-amine A 180-mL thick-walled glass pressure tube was charged with a mixture of N-(3-bromophenyl)phthalimide (1.94 g, 6.43 mmol), palladium(II) acetate (14.4 mg, 0.06 mmol), tri-o-tolylphosphine (78.3 mng, 0.26 mmol), triethylamine (4 mL, 28.70 mmol), N-methyl-N-(tert-butoxycarbonyl)-4-penten-2-amine (1.28 g, 6.43 mmol), and acetonitrile (6 mL). The tube was flushed with nitrogen and sealed. The mixture was stirred and heated at 115° C. (oil bath temperature) for 112 h. After cooling to ambient temperature, the resulting solid residue was diluted with water (20 ml,) and extracted with $CH_2Cl_2$ (4×20 mL). The combined $CH_2Cl_2$ extracts were washed with a saturated NaCl solution (30 mL), dried ($Na_2SO_4$), filtered, concentrated by rotary evaporation, and vacuum dried to give a viscous oil (3.00 g). The crude product was purified by column chromatography on silica gel (120 g, Merck 70–230 mesh) eluting with ethyl acetate-hexane (1:1, v/v). Selected fractions containing the product ($R_f$ 0.44) were combined, concentrated by rotary evaporation, and vacuum dried to give 1.01 g (37.3%) of a viscous, light-yellow oil. (E)-N-Methyl-5-(3-aminophenyl)-4-penten-2-amine Under a nitrogen atmosphere, a stirring ice-cold (0–5° C.) solution of (E)-N-methyl-N-(tert-butoxycarbonyl)-5-[(1-N-phthaloyl)-3-phenyl]-4-penten-2-amine (1.01 g, 2.40 mmol) in anisole (13 mL.) was treated dropwise over 10 min with trifluoroacetic acid (16.28 g, 142.8 mmol). After stirring at 0–5° C. for 45 min, the solution was concentrated by rotary evaporation, and the residue was further dried under vacuum. The resulting yellow syrup was treated with a 25% (w/w) solution of methylamine in ethanol (50 mL) and allowed to stir for 48 h. The mixture was concentrated on a rotary evaporator. The resulting residue was diluted with water (20 mL), treated with saturated NaCl solution (25 mL), and basified to pH 10 with 10% NaOH solution. The mixture was extracted with $CHCl_3$ (6×30 mL). The combined $CHCl_3$ extracts were dried ($Na_2SO_4$), filtered, and concentrated by rotary evaporation to produce a light-yellow oil (0.52 g). The crude product was purified by column chromatography on silica gel (Merck 70–230 mesh) eluting with $CHCl_3$—$CH_3OH$ (1:1, v/v, containing 2% (v/v) $Et_3N$). Selected fractions were combined and concentrated by rotary evaporation to give a light-yellow oil (0.271 g). The oil was further purified by column chromatography on silica gel containing 5 wt % silver nitrate (30 g, silica gel 60, Merck 9385) eluting with $CH_3OH$—$Et_3N$ (9:1, v/v). Selected fractions containing the product ($R_f$ 0.39) were combined and concentrated by rotary evaporation. The resulting brown oil was filtered through silica gel (12.5 g, Merck 70–230 mesh) eluting with $CH_3OH$—$Et_3N$ (9:1, v/v). The filtrate was concentrated by rotary evaporation. The resulting yellow oil was dissolved in $CHCl_3$, dried ($MgSO_4$), filtered, concentrated by rotary evaporation, and further dried under vacuum to give 0.15 g (32.7%) of a yellow oil.

Sample No. 3 exhibits a log P of 2.07, and such a favorable log P value indicates that the compound has the capability of passing the blood-brain barrier. The compound exhibits a Ki of 132 nM. The low binding constant indicates that the compound exhibits good high affinity binding to certain CNS nicotinic receptors.

Sample No. 3 exhibits an $EC_{50}$ value of 920 nM and an $E_{max}$ value of 78% for dopamine release, indicating that the compound effectively induces neurotransmitter release thereby exhibiting known nicotinic pharmacology.

Sample No. 3 exhibits an $E_{max}$ of 2% (at a concentration of 100 uM) at muscle-type receptors, indicating that the compound does not induce activation of muscle-type receptors. The sample exhibits an $E_{max}$ of 6% (at a concentration of 100 uM) at ganglionic-type receptors. The compound has the capability to activate human CNS receptors without activating muscle-type and ganglionic-type nicotinic acetylcholine receptors to any significant degree. Thus, there is provided a therapeutic window for utilization in the treatment of CNS disorders. That is, at certain levels the compound shows CNS effects to a significant degree but does not show undesirable muscle or ganglion effects to any significant degree.

The foregoing is illustrative of the present invention and is not to be construed as limiting thereof. The invention is defined by the following claims, with equivalents of the claims to be included therein.

That which is claimed is:

1. A compound having the formula:

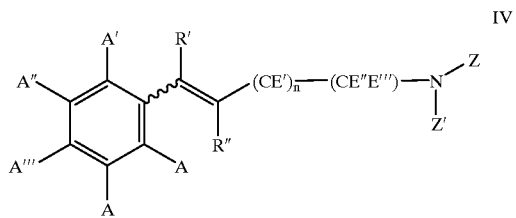

where $A^{IV}$ is NR'R"; A, $A^I$, $A^{II}$, $A^{III}$ and $A^{IV}$ are substituent species characterized as having a sigma m value between −0.3 and about 0.75; E, $E^I$, $E^{II}$, $E^{III}$, R', R", Z and $Z^I$ are individually hydrogen or lower alkyl; n is an integer from 1 to 5; and the wavy line in the structure indicates that the compound can have the cis (Z) or trans (E) form.

2. The compound of claim 1 wherein $A^{IV}$ is $NH_2$, $NHCH_3$ or $N(CH_3)_2$.

3. The compound of claim 1 wherein the compound has a trans (E) form, R' and R" both are hydrogen, E, $E^I$ and $E^{II}$ each are hydrogen, $E^{III}$ is hydrogen or lower alkyl, Z is hydrogen or methyl, and $Z^I$ is hydrogen.

4. The compound of claim 1, (E)-4-(3-aminophenyl)-3-buten-1-amine.

5. The compound of claim 1, (E)-N-methyl-4-(3-aminophenyl)-3-buten-1-amine.

6. The compound of claim 1, (E)-N-methyl-5-(3-aminophenyl)-4-penten-2-amine.

7. The compound of claim 1 wherein n is 1 or 2.

8. A pharmaceutical composition incorporating a compound having the formula:

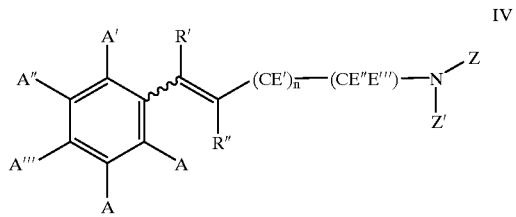

where $A^{IV}$ is NR'R"; A, $A^I$, $A^{II}$, $A^{III}$ and $A^{IV}$ are substituent species characterized as having a sigma m value between −0.3 and about 0.75; E, $E^I$, $E^{II}$, $E^{III}$, R', R", Z and $Z^I$ are individually hydrogen or lower alkyl; n is an integer from 1 to 5; and the wavy line in the structure indicates that the compound can have the cis (Z) or trans (E) form.

9. The pharmaceutical composition of claim 8 wherein $A^{IV}$ is $NH_2$, $NHCH_3$ or $N(CH_3)_2$.

10. The pharmaceutical composition of claim 8 wherein the compound has a trans (E) form, R' and R" both are hydrogen, E, $E^I$ and $E^{II}$ each are hydrogen, $E^{III}$ is hydrogen or lower alkyl, Z is hydrogen or methyl, and $Z^I$ is hydrogen.

11. The pharmaceutical composition of claim 1, (E)-4-(3-aminophenyl)-3-buten-1-amine.

12. The pharmaceutical composition of claim 1, (E)-N-methyl-4-(3-aminophenyl)-3-buten-1-amine.

13. The pharmaceutical composition of claim 1, (E)-N-methyl-5-(3-aminophenyl)-4-penten-2-amine.

14. The pharmaceutical composition of claim 1 wherein n is 1 or 2.

15. A method for treating a disorder comprising administering to a subject in need thereof, an effective amount of a compound of the formula:

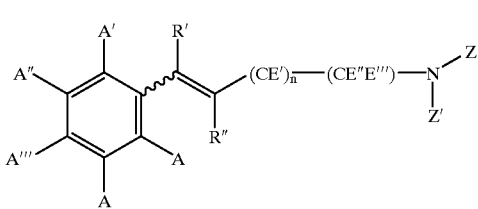

where $A^{IV}$ is NR'R"; A, A', A", A''' and $A^{IV}$ are substituent species characterized as having a sigma m value between −0.3 and about 0.75; E, $E^I$, $E^{II}$, $E^{III}$, R', R", Z and $Z^I$ are individually hydrogen or lower alkyl; n is an integer from 1 to 5; and the wavy line in the structure indicates that the compound can have the cis (Z) or trans (E) form.

16. The method of claim 15 whereby $A^{IV}$ is $NH_2$, $NHCH_3$ or $N(CH_3)_2$.

17. The method of claim 15 whereby the compound has a trans (E) form, R' and R" both are hydrogen, E, $E^I$ and $E^{II}$ each are hydrogen, $E^{III}$ is hydrogen or lower alkyl, Z is hydrogen or methyl, and $Z^I$ is hydrogen.

18. The method of claim 15 whereby the compound is (E)-4-(3-aminophenyl)-3-buten-1-amine.

19. The method of claim 15 whereby the compound is (E)-N-methyl-4-(3-aminophenyl)-3-buten-1-amine.

20. The method of claim 15 whereby the compound is (E)-N-methyl-5-(3-aminophenyl)-4-penten-2-amine.

21. The method of claim 15 whereby n is 1 or 2.

* * * * *

UNITED STATES PATENT AND TRADEMARK OFFICE
CERTIFICATE OF CORRECTION

PATENT NO. : 6,262,124 B1
DATED : July 17, 2001
INVENTOR(S) : Dull et al.

It is certified that error appears in the above-identified patent and that said Letters Patent is hereby corrected as shown below:

<u>Title page,</u>
Item [56], References Cited, should contain on "OTHER PUBLICATIONS" listing:
-- Beams, Richard M., et al., *Development of a Novel Series of Trialkoxyaryl Derivatives as Specific and Competitive Antagonists of Platelet Activating Factor*, J. MED. CHEM. (1995), 38(12), 2130-7, XP002121846 --; and
-- Olsen, David K., et al., *Preparation and stereochemistry of 4-aryl-3-butenylamines. A novel synthesis of an oxazolo "2, 3-a! isoindole*, J. ORG. CHEM., (1980), 45(20), 4049-52, XP002121847 --

In claims 1, 8, and 15, in the formulae depicted, the substituent "A" situated adjacent to the substituent denoted "A'''" on the six-membered ring should be -- $A^{IV}$ --.

Signed and Sealed this

First Day of July, 2003

JAMES E. ROGAN
*Director of the United States Patent and Trademark Office*